US007087715B2

(12) United States Patent
Zhou

(10) Patent No.: US 7,087,715 B2
(45) Date of Patent: Aug. 8, 2006

(54) HUMAN PARIS-1 ANTIGEN AND NUCLEIC ACIDS: DIAGNOSTIC AND THERAPEUTIC USES

(75) Inventor: Yaling Zhou, Rockville, MD (US)

(73) Assignee: Northwest Biotherapeutics, Inc., Bothell, WA (US)

( * ) Notice: Subject to any disclaimer, the term of this patent is extended or adjusted under 35 U.S.C. 154(b) by 207 days.

(21) Appl. No.: 10/221,658

(22) PCT Filed: Mar. 13, 2001

(86) PCT No.: PCT/US01/08083

§ 371 (c)(1),
(2), (4) Date: Sep. 13, 2002

(87) PCT Pub. No.: WO01/70244

PCT Pub. Date: Sep. 27, 2001

(65) Prior Publication Data

US 2003/0206908 A1   Nov. 6, 2003

Related U.S. Application Data

(60) Provisional application No. 60/190,361, filed on Mar. 16, 2000.

(51) Int. Cl.
*C07K 14/00* (2006.01)
(52) U.S. Cl. .................. 530/350; 536/23.1; 536/23.5; 536/24.3; 536/24.31; 536/24.33; 530/300
(58) Field of Classification Search ............ 536/23.5, 536/23.1, 24.3; 530/350, 300; 514/44
See application file for complete search history.

(56) References Cited

U.S. PATENT DOCUMENTS

| | | | |
|---|---|---|---|
| 6,774,216 B1 * | 8/2004 | Ruben et al. ............ 530/387.9 |
| 2001/0053519 A1 * | 12/2001 | Fodor et al. ................. 435/6 |
| 2003/0175739 A1 * | 9/2003 | Rosen et al. ................. 435/6 |
| 2005/0250180 A1 * | 11/2005 | Jacobs et al. .............. 435/69.1 |

OTHER PUBLICATIONS

Zhou et al. Biochem. Biophys. Res. Comm. 2002; 290: 830-8.*
Saijo et al. Cancer Sci. Oct. 2004; 95 (10): 772-6.*
Skolnick et al. Trends in Biotechnology. 2000; 18 (1): 34-9.*
Bowie et al. Science. 1990; 257: 1306-10.*
Kelland Eur. J. Cancer. Apr. 2004; 40 (6): 827-36.*
Verma et al. Nature 1997, 389: 239-42.*
Amalfitano et al. Current Gene Therapy 2002, 2: 111-33.*
Patterson AP. Memorandum (Jan. 14, 2003); pp. 1-3.*
Pandha et al. Current Opinion in Investigational Drugs 2000; 1 (1): 122-34.*
Gura (Science. 1997; 278: 1041-1042.*
Bergers et al. Current Opinion in Genetics and Development. 2000; 10: 120-7.*
Arbieva et al., "High-Resolution Physical Map And Transcript Identification Of Prostate Cancer Deletion Interval On 8p22," *Genome Res.* 10:244-257 (2000).
Boel et al., "BAGE: A New Gene Encoding An Antigen Recognized On Human Melanomas By Cytolytic T Lymphocytes," *Immunity* 2:167-175 (1995).
Borysiewicz et al., "A Recombinant Vaccinia Virus Encoding Human Papillomavirus Types 16 and 18, E6 and E7 Proteins As Immunotherapy For Cervical Cancer," *Lancet* 347:1523-1527 (1996).
Brass et al., "Translation Initiation Factor eIF-4gamma Is Encoded By An Amplified Gene And Induces An Immune Response In Squamous Cell Lung Carcinoma," *Hum. Mol. Genet.* 6:33-39 (1997).
Brichard et al., "The Tyrosinase Gene Codes For An Antigen Recognized By Autologous Cytolytic T Lymphocytes On HLA-A2 Melanomas," *J. Exp. Med.* 178:489-495 (1993).
Brinkmann et al., "*PAGE-1*, An X Chromosome-Linked *GAGE*-Like Gene That Is Expressed In Normal And Neoplastic Prostate, Testis, And Uterus," *Natl. Acad. Sci. USA* 95:10757-10762 (1998).
Carducci et al., "Prostate Cancer Treatment Strategies Based On Tumor-Specific Biological Principles: Future Directions," *Semin. Oncol.* 23:56-62 (1996).
Carey et al., "Cell Surface Antigens Of Human Malignant Melanoma: Mixed Hemadsorption Assays For Humoral Immunity To Cultured Autologous Melanoma Cells," *Proc. Natl. Acad. Sci. USA* 73:3278-3282 (1976).
Chen et al., "Isolation And Characterization Of *PAGE*-1 And *GAGE*-7," *J. Biol. Chem.* 273:17618-17625 (1998).
Cormier et al., "Enhancement Of Cellular Immunity In Melanoma Patients Immunized With A Peptide From MART-1/Melan A," *Cancer J. Sci. Am.* 3:37-44 (1997).

(Continued)

*Primary Examiner*—Stephen L. Rawlings
(74) *Attorney, Agent, or Firm*—Townsend and Townsend and Crew LLP

(57) ABSTRACT

The present invention relates to the discovery, identification and characterization of a novel tumor suppressor gene designated PARIS-1. The invention includes nucleotide sequences of the PARIS-1 gene and amino acid sequences of its encoded protein product(s), as well as fragments, derivatives and analogs thereof. The invention also includes the production of PARIS-1 proteins, fragments and derivatives and of antibodies specific for PARIS-1 gene products. The invention further comprises agents and compositions which can modulate the expression of PARIS-1 or PARIS-1 expression products to effect the proliferation of cells which express PARIS-1. One particular embodiment comprises agents and compounds which can slow or ablate the proliferation of prostate tumor cells.

5 Claims, 2 Drawing Sheets

OTHER PUBLICATIONS

Coulie et al., "A New Gene Coding For A Differentiation Antigen Recognized By Autologous Cytolytic T Lymphocytes On HLA-A2 Melanomas," *J. Exp. Med.* 180:35-42 (1994).

De Plaen et al., "Structure, Chromosomal Localization, And Expression Of 12 Genes Of The *MAGE* Family," *Immunogenetics* 40:360-369 (1994).

Falk et al., "Allele-Specific Motifs Revealed By Sequencing Of Self-Peptides Eluted From MHC Molecules," *Nature* 351:290-296 (1991).

Gaugler et al., "Human Gene MAGE-3 Codes For An Antigen Recognized On A Melanoma By Autologous Cytolytic T Lymphocytes," *J. Exp. Med.* 179:921-930 (1994).

Güre et al., "Human Lung Cancer Antigens Recognized By Autologous Antibodies: Defenition Of A Novel cDNA Derived From The Tumor Suppressor Gene Locus On Chromosome 3p21.3," *Cancer Res.* 58:1034-1041 (1998).

Horoszewicz et al., "LNCaP Model of Human Prostatic Carcinoma" *Cancer Res.* 43:1809-1818 (1983).

Hrouda et al., "Gene Therapy For Prostate Cancer," *Gene Ther.* 3:845-852 (1996).

Hsu et al., "Vaccination Of Patients With B-Cell Lymphoma Using Autologous Antigen-Pulsed Dendritic Cells," *Nat. Med.* 2:52-58 (1996).

Isaacs et al., "Molecular Biology Of Prostate Cancer," *Semin. Oncol.* 21:514-521 (1994).

Isaacs, "Molecular Genetics Of Prostate Cancer," *Cancer Surv.* 25:357-379 (1995).

Jäger et al., "Simultaneous Humoral and Cellular Immune Response Against Cancer-Testis Antigen NY-ESO-1: Definition of Human Histocompatibility Leukocyte Antigen (HLA)-A2-Binding Peptide Epitopes," *J. Exp. Med.* 187:265-270 (1998).

Kawakami et al., "Cloning Of The Gene Coding For A Shared Human Melanoma Antigen Recognized By Autologous T Cells Infiltrating Into Tumor," *Proc. Natl. Acad. Sci. USA* 91:3515-3519 (1994).

Kawakami et al., "Identification Of A Human Melanoma Antigen Recognized By Tumor-Infiltrating Lymphocytes Associated With *In Vivo* Tumor Rejection," *Proc. Natl. Acad. Sci. USA* 91:6458-6462 (1994).

Kim et al., "Dendritic Cells Infected With Poxviruses Encoding MART-1/Melan A Sensitive T Lymphocytes In Vitro," *J. Immunother.* 20:276-286 (1997).

Kozak, "At Least Six Nucleotides Preceding The AUG Initiator Codon Enhance Translation In Mammalian Cells," *J. Mol. Biol.* 196:947-950 (1987).

Kozak, "Possible Role Of Flanking Nucleotides In Recognition Of The AUG Initiator Codon By Eukaryotic Ribosomes," *Nuc. Acids. Res.* 9:5233-5252 (1981).

Landis et al., "Cancer Statistics,1999" *CA Cancer J. Clin.* 49:8-31 (1999).

Mandelboim et al., "CTL Induction By A Tumour-Associated Antigen Octapeptide Derived From A Murine Lung Carcinoma," *Nature* 369:67-71 (1994).

Mandelboim et al., "CTL Induction By A Tumour-Associated Antigen Octapeptide Derived From A Murine Lung Carcinoma," *Nature* 390:643 (1997).

McAneny et al., "Results Of A Phase 1 Trial Of A Recombinant Vaccinia Virus That Expresses Carcinoembryonic Antigen In Patients With Advanced Colorectal Cancer," *Ann. Surg. Oncol.* 3:495-500 (1996).

Nestle et al., "Vaccination Of Melanoma Patients With Peptide- Or Tumor Lystate-Pulsed Dendritic Cells," *Nat. Med.* 4:328-332 (1998).

Nupponen et al., "Genetic Alterations In Prostate Cancer Cell Lines Detected By Comparative Genomic Hybridization," *Cancer Genet. Cytogenet.* 101:53-57 (1998).

Pass et al., "Immunization Of Patients With Melanoma Peptide Vaccines: Immunologic Assessment Using The ELISPOT Assay," *Cancer J. Sci. Am.* 4:316-323 (1998).

Pfreundschuh et al., "Serological Analysis Of Cell Surface Antigens Of Malignant Human Brain Tumors," *Proc. Natl. Acad. Sci. USA* 75:5122-5126 (1978).

Ponder, "Inherited Predispositions To Cancer," *TIG* 6:213-218 (1990).

Reynolds et al., "HLA-Independent Heterogeneity of $CD8^+T$ Cell Responses To MAGE-3, Melan-A/Mart-1, gp100, Tyrosinase, MC1R, and TRP-2 In Vaccine-Treated Melanoma Patients," *J. Immunol.* 161:6970-6976 (1998).

Rosenberg et al., "Immunizing Patients With Metastatic Melanoma Using Recombinant Adenoviruses Encoding MART-1 or gp100 Melanoma Antigens," *J. Natl. Cancer Inst.* 90:1894-1900 (1998).

Rosenberg et al., "Immunologic And Therapeutic Evaluation Of A Synthetic Peptide Vaccine For The Treatment Of Patients With Metastatic Melanoma," *Nat. Med.* 4:321-327 (1998).

Royai et al., "Preclinical Model Of Prostate Cancer," *Semin. Oncol.* 23:35-40 (1996).

Sahin et al., "Human Neoplasms Elicit Multiple Specific Immune Responses In The Autologous Host," *Proc. Natl. Acad. Sci. USA* 92:11810-11813 (1995).

Salgaller et al., "Immunization Against Epitopes In The Human Melanoma Antigen gp100 Following Patient Immunization With Synthetic Peptides," *Cancer Res.* 56:4749-4757 (1996).

Scanlan et al., "Characterization Of Human Colon Cancer Antigens Recognized By Autologous Antibodies," *Int. J. Cancer* 76:652-658 (1998).

Shen et al., "Identification Of The Human Prostatic Carcinoma Oncogene PTI-1 By Rapid Expression Cloning And Differential RNA Display," *Proc. Natl. Acad. Sci. USA* 92:6778-6782 (1995).

Shiku et al., "Cell Surface Antigens Of Human Malignant Melanoma, II. Serological Typing With Immune Adherence Assays and Definitions of Two New Surface Antigens" *J. Exp. Med.* 144:873-881 (1976).

Small, "Prostate Cancer," *Curr. Opin. Oncol.* 9:277-286 (1997).

Smith et al., "Single-Step Purification Of Polypeptides Expressed In *Escherichia Cells* As Fusions With Glutathione S-Transferase," *Gene* 6:31-40 (1988).

Song et al., "Dendritic Cells Genetically Modified With An Adenovirus Vector Encoding The cDNA For A Model Antigen Induce Protective And Therapeutic Antitumor Immunity," *J. Exp. Med.* 8:1247-1256 (1997).

Spagnoli et al., "Peptide-Specific CTL In Tumor-Infiltrating Lymphocytes From Metastatic Melanomas Expressing *MART-1/Melan-A, gp100* And *Tyrosinase* GENES: A Study In An Unselected Group Of HAL-A2.1-Positive Patients," *Int. J. Cancer* 64:309-315 (1995).

Su et al., "Surface-Epitope Masking And Expression Cloning Identifies The Human Prostate Carcinoma Tumor Antigen Gene PCTA-1 A Member Of The Galectin Gene Family," *Proc. Natl. Acad. Sci USA* 93:7252-7257 (1996).

Sun et al., "Human Prostatic Carcinoma Oncogene *PTI-1* Is Expressed In Human Tumor Cell Lines And Prostate Carcinoma Patient Blood Samples," *Cancer Res.* 57:18-23 (1997).

Türeci et al., "The *SSX-2* Gene, Which Is Involved In The t(X;18) Translocation Of Synovial Sarcomas, Codes for the Human Tumor Antigen HOM-MEL-40" *Cancer Res*, 56:4766-4772 (1996).

Türeci et al., "Serological Analysis Of Human Tumor Antigens: Molecular Definition And Implications," *Mol. Med. Today* 3:342-349 (1997).

Türeci et al., "Molecular Definition Of A Novel Human Galectin Which Is Immunogenic In Patients With Hodgkin's Disease," *J. Biol.Chem.* 10:6416-6422 (1997).

Ueda et al., "Cell Surface Antigens Of Human Renal Cancer Defined By Autologous Typing," *J. Exp. Med.* 150:564-579 (1979).

Van Bleek et al., "Isolation Of An Endogenously Processed Immunodominant Viral Peptide From The Class I H-2K$^b$ Molecule," *Nature* 348:213-216 (1990).

Van Der Bruggen et al., "A Gene Encodign An Antigen Recognized By Cytolytic T Lymphocytes On A Human Melanoma," *Science* 254:1643-1647 (1991).

Weber et al., "Molecular Carcinogenisis Of Prostate Cancer: Potential Clinical Relevance And Nursing Implications," *Semin. Oncol. Nurs.,* 13:99-107 (1997).

Weinberg, "Tumor Supressor Genes," *Science* 254:1138-1146 (1991).

Xue et al., "Induction Of Human Cytotoxic T Lymphocytes Specific For Prostate-Specific Antigen," *Prostate* 30:73-78 (1997).

Yang et al., "Identification Of Genes Expressed Differentially by LNCaP or PC-3 Prostate Cancer Cell Lines," *Cancer Res.* 58:3732-3735 (1998).

Yin et al., "Limiting The Location Of A Putative Human Prostate Cancer Tumor Suppressor Gene At Chromosome 13q14.3," *Oncogene* 18:7576-7583 (1999).

Zou et al., "p53 Regulates The Expression Of The Tumor Suppressor Gene Maspin," *J. Biol. Chem.* 275:6061-6054 (2000).

\* cited by examiner

P9E: 5'- GGACGAAGTACAACGAGAAG-3'
P9F: 5'- TACCCTATAGAGGCAGTGCT-3'

HUMAN PARIS-1 ANTIGEN AND NUCLEIC ACIDS: DIAGNOSTIC AND THERAPEUTIC USES

BACKGROUND OF THE INVENTION

The present invention relates to the discovery, identification and characterization of a novel tumor suppressor gene PARIS-1 ("Prostate Antigen Recognized and Identified by SEREX"-1). The invention encompasses nucleotide sequences of the PARIS-1 gene and amino acid sequences of its encoded protein product(s), as well as derivatives and analogs thereof. The invention also encompasses the production of PARIS-1 proteins and antigen specific antibodies. The invention further encompasses compositions and methods for diagnostic and therapeutic applications for prostate cancer.

Prostate cancer is the most commonly diagnosed cancer in men in the United States and around the world. It accounts for 29% of all cancers in men in the United States and is one of the most frequent causes of cancer death in men throughout the world. This year, approximate 179,300 new cases of prostate cancer are expected to be diagnosed and approximately 37,000 will succumb to their disease (Landis et al., *CA Cancer J Clin.* 49:8–31 (1999)). Still, the number of cases of prostate cancer in the year 2000 and beyond are expected to increase (Boyle, In, *First International Consultation on Prostate Cancer*, Monaco, Jun. 20–Jun. 22 1996, pp. 1–30). Thus, prostate cancer will remain as a serious public health concern in the United States and around the world.

Tumor suppressor genes play an important role in normal cell growth, differentiation and progression through the cell cycle. Tumor suppressor genes in humans have been identified through studies of genetic changes in occurring in cancer cells (Ponder, *Trends Genet.* 6:213–218 (1990); Weinberg, *Science* 254:1138–1146 (1991)). Mutations that cause change in gene expression of tumor suppressor genes lead to cell transformation in vitro and tumor development in vivo. It has been documented that loss of tumor suppressor(s) genes at chromosome 10, chromosome 8, chromosome 13, or mutations in p53 could be events leading to prostate cancer (Arbieva et al., *Genome Res.* 10:244–257 (2000); Yin et al., *Oncogene* 18:7576–7583 (1999); Zou et al., *J. Biol. Chem.* 275:6051–6054 (2000)). The exact series of events involving tumor suppressor genes that lead to initiation and progression of cancer is not known.

Prostate cancer is a slow growing disease and possesses a multiple-step nature during the process of its carcinogenesis. It usually starts as a localized benign disease, then advances gradually into metastasis, and eventually develops into a hormone resistant cancer (Small, *Curr. Opin. Oncol.* 9:277–286 (1997); Weber, *Semin. Oncol. Nurs.*, 13:99–107 (1997); Carducci, et al., *Semin. Oncol.* 23:56–62 (1996); Royai, et al., *Semin. Oncol.* 23:35–40 (1996)). The progression of the cancer is accompanied by a series of morphological, histological and pathological changes. A number of genetic alterations have also been observed during the progression of prostate cancer, as described above and further inactivation of tumor suppressor genes, such as p53, Rbl, PTEN, DCC, and KAI, mutation of oncogenes such as Ras, loss of heterozygosity on certain chromosome loci such chromosome 8p, 10q, 16q, 17p, and 18q, and suppression of certain gene expression such as E-cadherin/a-catenin (Small, supra; Weber, supra; Carducci et al., supra; Isaacs, *Cancer Surv.* 25:357–379 (1995); Isaacs, et al., *Semin. Oncol.* 21:514–521 (1994); Hrouda, et al., *Gene Ther.* 3:845–852 (1996); Nupponen, et al., *Cancer Genet. Cytogenet.* 101: 53–57 (1998)).

The search for tumor-specific or -associated antigens that induce specific immune responses in cancer patients remains a challenge in tumor immunology. Significant efforts have been made during the past decades in developing efficient strategies for identification of tumor-specific and -associated antigens, and a number of strategies including both immunological and non-immunological strategies have been developed and used for tumor-specific and -associated antigen identification. The immunological approaches most commonly used include: (1) a genetic approach based on the recognition of expressed tumor-specific or -associated antigens by autologous tumor-specific cytotoxic T lymphocyte CTL clones (van der Bruggen, et al., *Science* 254:1643–1647 (1991)); (2) a biochemical approach based on the acid elution of antigenic peptide bound to Major Histocompatibility Complex (MHC) class I molecules from tumor cells (Mandelboim, et al., *Nature* 369:67–71 (1994), (published erratum appears in *Nature* 390:643 (1997)); Falk, et al., *Nature* 351:290–296 (1991); Van Bleek, et al., *Nature* 348:213–216 (1990)); and (3) a serological approach, also known as autologous typing, based on the use of autologous serum to detect cell-surface antigens on the tumor cells of cancer patients (Pfreundschuh, et al., *Proc. Natl. Acad. Sci. USA* 75:5122–5126 (1978); Shiku, et al., *J. Exp. Med.* 144.873–881 (1976); Ueda, et al., *J. Exp. Med.* 150:564–579 (1979).

Using such approaches, a number of human tumor antigens have been identified from several tumor types (Van der Bruggan, supra; Mandeboim, supra; Falk, supra; Van Bleek and Nathenson, supra; Boel, et al., *Immunity* 2:167–175 (1995); Brichard, et al., *J. Exp. Med.* 178:489–495 (1993); Coulie, et al., *J. Exp. Med.* 180:35–42 (1994); Kawakami, et al., *Proc. Natl. Acad. Sci. USA* 91:6458–6462 (1994); Kawakami, et al., *Proc. Natl. Acad. Sci. USA.* 91:3515–3519 (1994); Xue, et al., *Prostate* 30:73–78 (1997)). Both animal tumor models and human clinical trials have been developed to evaluate the identified tumor antigens in prevention and treatment of a variety of cancers. T cell responses have been detected, and some clinical benefits observed for some of the antigens. (Salgaller, et al., Cancer Res. 56:4749–4757 (1996); Hsu, et al., *Nat. Med.* 2:52–58 (1996); Borysiewicz, et al., *Lancet* 347:1523–1527 (1996); McAneny, et al., *Ann. Surg. Oncol.* 3:495–500 (1996); Cormier, et al., *Cancer J. Sci. Am.* 3:37–44 (1997); Pass, et al., *Cancer J. Sci. Am.* 4:316–323 (1998); Reynolds, et al., *J. Immunol.* 161:6970–6976 (1998); Rosenberg, et al., *Nat. Med.* 4:321–327 (1998); Rosenberg, et al., *J. Natl. Cancer Inst.* 90: 1894–1900 (1998); Spagnoli, et al., *Int. J. Cancer* 64:309–315 (1995); Kim, et al., *J. Immunother.* 20:276–286 (1997); Nestle, et al., *Nat. Med.* 4:328–332 (1998); Song, et al., *J. Exp. Med.* 186:1247–1256 (1997)).

However, all these approaches have encountered limitations in their further application and expansion to a broader range of tumor types. For example, defining T cell-recognized tumor antigens often depended on the pre-establishment of stable CTL clones that are often difficult to establish. Using autologous cell lines limits analysis to tumor cells that could be adapted to growth in vitro with some regularity such as melanoma (Shiku, supra; Carey, et al., *Proc. Natl. Acad. Sci. USA* 73:3278–282 (1976)), renal cancer (Ueda, supra), and brain cancer (Pfrunschuh, supra). Non-immunological strategies, including recently developed approaches such as differential display, subtractive cloning/hybridization, DNA microarray, are based solely on the differential expression of genes between tumor cells and their normal counterparts, or purely on computer analysis of the GenBank database such as database mining. The gene products identified by these approaches may be used as markers for diagnosis. However, their candidacy for use in immunotherapy remains unknown because no information on their antigenicity and immunogenicity is obtained by using these approaches.

Serological identification of antigens by Recombinant Expression cloning (SEREX) has emerged in recent years as a novel approach for identifying tumor antigens (Sahin, et al., *Proc. Natl. Acad. Sci. USA* 92:11810–11813 (1995)). This approach utilizes autologous patient sera to search for tumor antigens expressed in bacteria *Escherichia coli*, which are infected with lambda phages containing cDNA libraries prepared from fresh tumor tissues. Thus, this new approach bypasses both requirements for the pre-establishments of stable cytotoxic T lymphocyte (CTL) clones or tumor-infiltrating lymphocytes (TIL), and established tumor cell lines. The use of SEREX technology in identification of human tumor antigens has been successful in a number of tumor types, including melanoma (Sahin, supra; Tureci, et al., *Cancer Res.* 56:4766–4772 (1996)), renal cancer (Sahin, supra; Tureci, et al., *Mol. Med. Today* 3:342–349 (1997), astrocytoma (Sahin, supra), Hodgkin's disease (Sahin, supra; Tureci, et al., *J. Biol. Chem.* 272:6416–6422 (1997)), esophageal cancer (Sahin, supra), lung cancer (Brass, et al., *Hum. Mol. Genet.* 6:33–39 (1997); Gure, et al., *Cancer Res.* 58:1034–1041 (1998)), and colon cancer (Scanlan, et al., *Int. J. Cancer* 76:652–658 (1998), and a number of tumor specific or associated antigens have been identified from these cancers.

The tumor antigens identified by SEREX are immunogenic and are good candidates for agents in the treatment of cancer, including vaccines, when the cognate T cell epitopes are discerned. The ability of a SEREX-identified antigen to be recognized by CTLs has been demonstrated in a recent study showing that the peptide epitopes derived from a SEREX-identified tumor antigen NY-ESO-1 were recognized by CTLs from a patient with high NY-ESO-1 antibody titers (Jager, et al., *J. Exp. Med.* 187:265–270 (1998)). Moreover, some of the SEREX-identified tumor antigens such as MAGE-1, MAGE-3, MAGE-4 and tyrosinase had also been previously identified by the CTL approach (Brichard, supra; Gaugler, et al., *J. Exp. Med.* 179:921–930 (1994); De Plaen, et al., *Immunogenetics* 40:360–369 (1994)).

Prostate tumor antigens identified recently by using molecular approaches such as differential display or subtractive cloning include prostatic carcinoma oncogene PTI-1 (Shen, et al., *Proc. Natl. Acad. Sci. USA* 92:6778–6782 (1995); Sun, et al., *Cancer Res.* 57:18–23 (1997)), prostate carcinoma tumor antigen PCTA-1 (Su, et al., *Proc. Natl. Acad. Sci. USA* 93:7252–7257 (1996)); NPC-1 (Yang, et al., *Cancer Res.* 58:3732–3735 (1998)); PAGE-1 and GAGE-7 (Brinklmann, et al., *Proc. Natl. Acad. Sci. USA* 95:10757–10762 (1998); Chen, et al., *J. Biol. Chem.* 273: 17618–17625 (1998)). Some of these antigens displayed a pattern of restricted expression in prostate or prostate cancer cells, but it is crucial to point out that none have been shown to induce either cellular or humoral immune responses. Thus, the possibility of using these antigens for the specific immunotherapy of prostate cancer remains unclear. Therefore, there continues to exist a need for identifying additional antigens associated with prostate tissue or tumor antigens that are useful as agents to treat hyperplastic and malignant conditions that are either immunogenic and capable of acting as tumor-rejection antigens or that function to suppress tumor development in prostate cancer patients.

SUMMARY OF THE INVENTION

The present invention relates to the discovery, identification and characterization of a novel tumor suppressor gene, PARIS-1 (Prostate Antigen Recognized and Identified by SEREX (Serological identification of antigens by recombinant expression cloning)). PARIS-1, described for the first time herein, was found to be expressed at high levels in normal prostate tissue and at very low levels in several prostate tumor cell lines and primary prostate tumors. The present invention encompasses nucleotide sequences of the PARIS-1 gene, and amino acid sequences of its encoded protein, as well as derivatives, biologically active fragments) and analogs thereof. The nucleotide sequences of the present invention encompass nucleotide sequences of the human PARIS-1 gene (hPAIR-1) (SEQ ID NO: 3) and PARIS-1 homologs of other species. The present invention also relates to nucleic acids hybridizable to or complementary to the foregoing nucleotide sequences. In a specific embodiment, PARIS-1 is a human gene which encodes the protein depicted as SEQ ID NO: 4, and the PARIS-1 protein is a human protein as depicted, for example, as SEQ ID NO: 4. In a specific embodiment the nucleotide sequence of human PARIS-1 is as depicted as SEQ ID NO: 3.

The present invention also encompasses fragments of PARIS-1, and derivatives and analogs thereof, which comprise one or more domains of a PARIS-1 protein. The invention further encompasses antibodies to PARIS-1 and PARIS-1 derivatives and analogs. The invention still further encompasses methods for the production of PARIS-1 protein fragments, derivatives and analogs.

The present invention also encompasses methods for the use of agents and compositions based on PARIS-1 proteins and nucleic acids for modulating cell proliferation and as a diagnostic. Agents and compounds of the invention include but are not limited to PARIS-1 proteins and analogs and derivatives (including biologically active fragments) thereof; antibodies thereto; nucleic acids encoding the PARIS-1 proteins, fragments, analogs, or derivatives; and PARIS-1 antisense nucleic acids.

The invention encompasses methods for administering agents which slow or stop disorders of overproliferation, (e.g., cancer and hyperproliferative disorders); which agents enhance or promote PARIS-1 activity (e.g., PARIS-1, an agonist of PARIS-1; nucleic acids that encode PARIS-1).

The invention also provides methods for the administration of administering agents and compounds that decrease or antagonize (inhibit) PARIS-1 function (e.g., antibodies, antisense nucleic acids, ribozymes and triple helix molecules) to modulate disorders involving deficient cell proliferation (growth) or in which cell proliferation is otherwise desired (e.g., degenerative disorders, growth deficiencies, lesions, physical trauma).

The invention also encompasses animal models, diagnostic methods and screening methods for predisposition to disorders, and methods to identify agents which act as PARIS-1 agonists and antagonists.

DESCRIPTION OF THE SPECIFIC EMBODIMENTS

Figure 1:
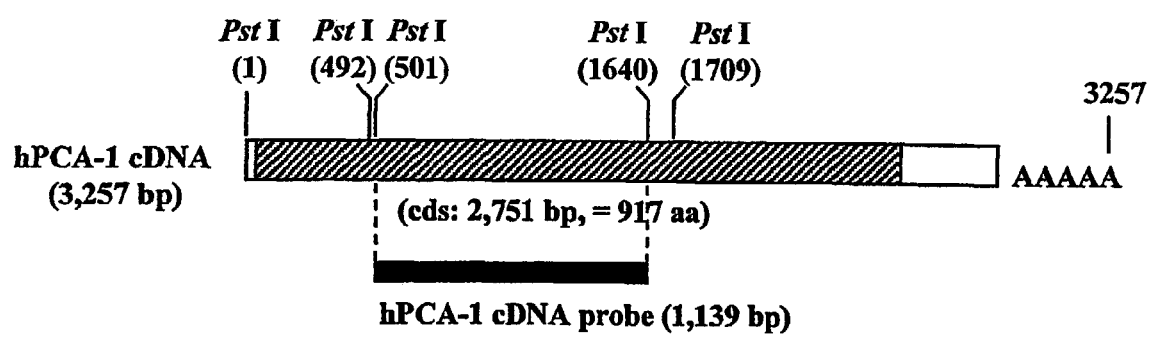
FIG. 1 is a schematic representation of the human PARIS-1 cDNA structure and the location of the human PARIS-1 cDNA probe used in Northern blot hybridization. The stripped box indicates the protein-coding region. The human PARIS-1 probe is a 1,139 bp PstI fragment (black box) within the protein-coding region. The positions of PstI restriction sites, and the location of the probe are indicated.

The present invention relates to methods, agents and compositions for the diagnosis and treatment of prostate cancer which utilize isolated polynucleotides corresponding to the PARIS-1 gene (Prostate Antigen Recognized and Identified by SEREX), proteins encoded by the PARIS-1 gene (SEQ ID NO: 3) and antigenic and immunogenic fragments thereof. Antibodies and recombinant antigen binding molecules capable of specifically recognizing and binding to PARIS-1 protein are also encompassed by the present invention. The human PARIS-1 gene (SEQ ID NO: 3) encodes a predicted 917 amino acid protein (SEQ ID NO:4) containing several sites for potential post-translational modification, including sites for N-linked glycosylation, cAMP- and cGMP-dependent protein kinase phosphorylation, protein kinase C phosphorylation, and casein kinase II phosphorylation. The protein is expressed in normal human prostate, liver, kidney, heart and colon tissue at high to moderate levels and at reduced levels in prostate cancer cell lines and prostate tumor tissue suggesting PARIS-1 acts as a tumor suppressor gene whose expression may play a role in maintaining the homeostatic growth of prostate cells in vivo. PARIS-1 does not appear to be similar in amino acid sequence or in structure to any protein previously identified.

The invention is based, in part, on the isolation of a cDNA fragment corresponding to the PARIS-1 gene by SEREX (Serological identification of the antigen by Recombinant Expression) cloning and upon the detailed molecular and biochemical characterization studies described in the Examples. The isolated cDNA fragment, clone P9, expressed in a library from a cancer cell line, was initially identified by reactivity with a serum pool of prostate cancer patients. Additional screening was accomplished with individual patient serum and normal serum. Several phage clones from the expression library were identified as comprising the same gene fragment as clone P9. Northern blot analysis revealed that PARIS-1 expressed by clone 9 was present in normal prostate cells and in certain other normal cells. It has also been determined that expression of PARIS-1 mRNA is reduced in prostate cancer cell lines.

The invention also encompasses agonists and antagonists of PARIS-1, including small molecules, large molecules, mutant PARIS-1 proteins that compete with native PARIS-1, and antibodies, as well as nucleotide sequences that can be used to inhibit PARIS-1 gene expression (i.e., antisense and ribozyme molecules, and gene or regulatory sequence replacement constructs) or to enhance PARIS-1 gene expression (i.e., expression constructs that place the PARIS-1 gene under the control of a strong promoter system), and transgenic animals that express a PARIS-1 transgene or "knockouts" that do not express PARIS-1.

In addition, the present invention encompasses methods, agents and compositions for the diagnostic evaluation, typing and prognosis of cancers and tumors, in particular, prostate tumors, and for the identification of subjects having a predisposition to such conditions. For example, PARIS-1 nucleic acid molecules of the invention can be used as diagnostic hybridization probes or as primers for diagnostic PCR analysis for the identification of PARIS-1 gene mutations, allelic variations and regulatory defects in the PARIS-1 gene.

The present invention further provides for diagnostic kits for the practice of such methods. Further, the present invention also relates to methods for the use of the PARIS-1 gene and/or PARIS-1 gene products for the identification of agents and compounds which modulate, i.e., act as agonists or antagonists, of PARIS-1 gene expression and or PARIS-1 gene product activity. Such compounds can be administered to an individual for use in the treatment of disorders of cellular overproliferation and, in particular, as agents for the ablating or slowing the growth of prostate tumors.

Various aspects of the invention are described in greater detail in the subsections below.

The PARIS-1 Gene:

The invention relates to the nucleotide sequences of PARIS-1 nucleic acids. In specific embodiments, PARIS-1 nucleic acids comprise the cDNA sequence as depicted as SEQ ID NO: 3, or the coding regions of PARIS-1, or nucleotide sequences encoding a PARIS-1 protein as depicted as SEQ ID NO: 4. The invention provides purified nucleic acids consisting of at least 6 contiguous nucleotides (i.e., a hybridizable portion) of a PARIS-1 sequence; in other embodiments, the nucleic acids consist of at least 8 (continuous) nucleotides, 25 nucleotides, 50 nucleotides, 100 nucleotides, 150 nucleotides, 200 nucleotides, or even up to 250 nucleotides of a PARIS-1 sequence. In another embodiment, the nucleic acids are smaller than 200 or 250 nucleotides in length. The nucleic acids can be single or double stranded. The invention also relates to nucleic acids hybridizable to/or complementary to the foregoing sequences. In specific aspects, nucleic acids are provided which comprise a sequence complementary to at least 10, 25, 50, 100, 200, or 250 nucleotides of a PARIS-1 gene. In a specific embodiment, a nucleic acid which is hybridizable to a PARIS-1 nucleic acid (e.g., having sequence SEQ ID NO: 3), or to a nucleic acid encoding a PARIS-1 derivative, under conditions of low stringency is provided.

By way of example and not limitation, procedures using such conditions of low stringency are as follows (see, Shilo and Weinberg, *Proc. Natl. Acad. Sci. USA* 78:6789–6792 (1981): Filters containing DNA are pretreated for 6 h at 40° C. in a solution containing 35% formamide, 5×SSC, 50 mM Tris-HCl (pH 7.5), 5 mM EDTA, 0.1% PVP, 0.1% FICOLL, 1% Bovine Serum Albumin (BSA), and 500 µg/ml denatured salmon sperm DNA. Hybridizations are carried out in the same solution with the following modifications: 0.02% PVP, 0.02% FICOLL, 0.2% Bovine Serum Albumin (BSA), 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which can be used are well known in the art (e.g., as employed for cross-species hybridizations).

In another specific embodiment, a nucleic acid which is hybridizable to a PARIS-1 nucleic acid under conditions of high stringency is provided. By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% FICOLL, 0.02% Bovine Serum Albumin (BSA), and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% FICOLL, and 0.01% Bovine Serum Albumin (BSA). This is followed by a wash in 0.1×SSC at 50° C. for 45 min before autoradiography. Other conditions of high stringency which can be used are well known in the art.

In another specific embodiment, a nucleic acid, which is hybridizable to a PARIS-1 nucleic acid under conditions of moderate stringency is provided. By way of example and not limitation, procedures using such conditions of moderate stringency are as follows: Prehybridization of filters containing DNA is carried out for 8 h to overnight at 55° C. in buffer composed of 6×SSC, 50 mM Tris-HCl (pH 7.5), 1mM EDTA, 0.02% PVP, 0.2% FICOLL, 0.02% BSA and 500 µg/ml denatured salmon sperm DNA. Filters are hybridized for 24 h at 55° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% FICOLL, and 0.01% BSA.

Various other stringency conditions which promote DNA hybridization can be used. For example, hybridization in 6×SSC at about 45° C., followed by washing in 2×SSC at 50° C. can be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5 M NaHPO$_4$ (pH7.2)/1 mM EDTA/7% SDS, or hybridization in 50% formamide/0.25 M NaHPO$_4$ (pH 7.2)/0.25 M NaCl/1 mM EDTA/7% SDS; followed by washing in 40 mM NaHPO$_4$ (pH 7.2)/1 mM EDTA/5% SDS at 50° C. or in 40 mM NaHPO$_4$ (pH7.2)/1 mM EDTA/1% SDS at 50° C. Both temperature and salt can be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., *Molecular Cloning, A Laboratory Manual*, Second Edition, Cold Spring Harbor Press, N.Y., pp. 9.47–9.57 (1989); and Ausubel et al., *Current Protocols in Molecular Biology*, Green Publishing Associates and Wiley Interscience, N.Y. (1989)).

Nucleic acids encoding derivatives and analogs of PARIS-1 proteins, and PARIS-1 antisense nucleic acids are additionally provided. As is readily apparent, as used herein, a "nucleic acid encoding a fragment or portion of a PARIS-1 protein" shall be construed as referring to a nucleic acid encoding only the recited fragment or portion of the PARIS-1 protein and not the other contiguous portions of the PARIS-1 protein as a continuous sequence. Fragments of PARIS-1 nucleic acids encoding one or more PARIS-1 domains are provided. Specific embodiments for the cloning of a PARIS-1 gene, presented as a particular example but not by way of limitation, follow.

For expression cloning (a technique commonly known in the art), an expression library is constructed by methods well known to the skilled artisan. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed PARIS-1 product. In one embodiment, anti-PARIS-1 specific antibodies can be used for selection.

In another embodiment, polymerase chain reaction (PCR) can be used to amplify the desired sequence in a genomic or cDNA library, prior to selection. Oligonucleotide primers representing known PARIS-1 sequences, e.g., as selected from SEQ ID NO: 3, can be used as primers in PCR. In a typical embodiment, the oligonucleotide primers represent at least part of the PARIS-1 conserved segments of strong homology, similarity or identity between PARIS-1 of different species. The synthetic oligonucleotides can be utilized as primers to amplify by PCR sequences from a source (RNA or DNA), typically a cDNA library, of potential interest. PCR can be carried out, (e.g., by use of a Perkin-Elmer Cetus thermal cycler and Taq polymerase (GENE AMP)). The DNA being amplified can include mRNA or cDNA or genomic DNA from any eukaryotic species. One of skill in the art can choose to synthesize several different degenerate primers, for use in the PCR reactions.

It is also possible to vary the stringency of hybridization conditions used in priming the PCR reactions, to allow for greater or lesser degrees of nucleotide sequence similarity between the known PARIS-1 nucleotide sequence and the related nucleic acid being isolated. For cross species hybridization, low stringency conditions are typically used. For same species hybridization, moderately stringent conditions are more typically used. After successful amplification of a segment of a related PARIS-1 nucleic acid, that segment can be molecularly cloned and sequenced, and utilized as a probe to isolate a complete cDNA or genomic clone. This, in turn, can permit the determination of the gene's complete nucleotide sequence, the analysis of its expression, and the production of its protein product for functional analysis, as described infra. In this fashion, additional genes encoding PARIS-1 proteins and PARIS-1 protein analogs can be identified.

The above-methods are not meant to limit the following general description of methods by which clones of PARIS-1 can be obtained. Any eukaryotic cell potentially can serve as the nucleic acid source for the molecular cloning of the PARIS-1 gene. The nucleic acid sequences encoding PARIS-1 can be isolated from vertebrate sources including, mammalian sources such as, porcine, bovine, feline, avian, equine, canine, human as well as additional primate sources, avian, reptilian, amphibian, piscine, and the like, from non-vertebrate sources, such as insects, from plants, and the like. The DNA can be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., *Molecular Cloning, A Laboratory Manual*, Second Edition, Cold Spring Harbor Laboratory Press, Cold Spring Harbor, N.Y. (1989); Glover, (ed.), *DNA Cloning: A Practical Approach*, MRL Press, Ltd., Oxford, U.K. Vol. I, II. (1985)). Clones derived from genomic DNA can contain regulatory and intron DNA regions in addition to coding regions; clones derived from cDNA will contain only exon sequences. Whatever the source, the gene can be molecularly cloned into a suitable vector for propagation of the gene.

In the molecular cloning of the gene from genomic DNA, DNA fragments are generated, some of which will encode the PARIS-1 gene. The DNA can be cleaved at specific sites using various restriction enzymes. Alternatively, one can use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene can be accomplished in a number of ways. For example, a portion of a PARIS-1 (of any species) gene or its specific RNA, or a fragment thereof can be purified and labeled, the generated DNA fragments can be screened by nucleic acid hybridization to the labeled probe (Benton and Davis *Science* 196:180–182 (1975); Grunstein and Hogness *Proc. Natl. Acad. Sci. USA* 72:3961–3965 (1975)). Those DNA fragments with substantial identity to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the gene can be detected by assays based on the physical, chemical, or immunological properties of its expressed product. For example, cDNA clones, or DNA clones which hybrid-select the proper mRNAs, can be selected which produce a protein that, i.e., has similar or identical electrophoretic migration, isoelectric focusing behavior, proteolytic digestion maps, promotion of cell proliferation activity, substrate binding activity, or antigenic properties as known for PARIS-1. Immune serum or an antibody which specifically binds to PARIS-1 can be used to identify putatively PARIS-1 synthesizing clones by binding in an ELISA (enzyme-linked immunosorbent assay) -type procedure.

The PARIS-1 gene can also be identified by mRNA selection by nucleic acid hybridization followed by in vitro translation. In this procedure, fragments are used to isolate complementary mRNAs by hybridization. Such DNA fragments represent available, purified PARIS-1 DNA of another species (e.g., human, mouse, and the like). Immunoprecipitation analysis or functional assays (i.e., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs can be selected by adsorption of polysomes isolated from cells to immobilized antibodies specifically directed against PARIS-1 protein. A radiolabeled PARIS-1 cDNA can be synthesized using the selected mRNA (from the adsorbed polysomes) as a template. The radiolabeled mRNA or cDNA can then be used as a probe to identify the PARIS-1 DNA fragments from among other genomic DNA fragments.

Alternatives to isolating the PARIS-1 genomic DNA include, but are not limited to, chemically synthesizing the gene sequence itself from a known sequence or making cDNA to the mRNA which encodes the PARIS-1 protein. For example, RNA for cDNA cloning of the PARIS-1 gene can be isolated from cells which express PARIS-1. Other methods are possible and are considered within the scope of the invention.

The identified and isolated PARIS-1 gene can then be inserted into an appropriate cloning vector. A large number of vector-host systems known in the art can be used. Possible vectors include, but are not limited to, plasmids or modified viruses, but the vector system must be compatible with the host cell used. Representative vectors include, but are not limited to, bacteriophage such as lambda derivatives, or plasmids such as pBR322 or pUC plasmid derivatives or the Bluescript vectors (Stratagene) to name but a few. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can comprise specific chemically synthesized oligonucleotides encoding restriction endonuclease recognition sequences. In an alternative method, the cleaved vector and PARIS-1 gene can be modified by homopolymeric tailing. Recombinant molecules can be introduced into host cells via transformation, transfection, infection, electroporation, and the like, so that many copies of the gene sequence are generated.

In an alternative method, the PARIS-1 gene can be identified and isolated after insertion into a suitable cloning vector in a "shot gun" approach. Enrichment for the PARIS-1 gene, for example, by size fractionization, can be done before insertion into the cloning vector. In specific embodiments, transformation of host cells with recombinant DNA molecules that incorporate the isolated PARIS-1 gene, cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA.

The PARIS-1 sequences provided by the present invention include those nucleotide sequences encoding substantially the same amino acid sequences as found in native human PARIS-1 proteins (SEQ ID NO: 4), and those encoded amino acid sequences with functionally equivalent amino acids, as well as those encoding other PARIS-1 derivatives or analogs.

Expression of the PARIS-1 Gene:

The nucleotide sequence coding for a PARIS-1 protein or a functionally active analog or fragment or other derivative thereof, can be inserted into an appropriate expression vector, (i.e., a vector which contains the necessary elements for the transcription and translation of the inserted protein-coding sequence). The necessary transcriptional and translational signals can also be supplied by the native PARIS-1 gene and/or its flanking regions. A variety of host-vector systems can be utilized to express the protein-coding sequence. These include but are not limited to, mammalian cell systems infected with virus (e.g., vaccinia virus, adenovirus, and the like); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities.

Depending on the host-vector system utilized, any one of a number of suitable transcription and translation elements can be used. In specific embodiments, the human PARIS-1 gene is expressed, or a nucleic acid sequence encoding a functionally active portion of human PARIS-1. In yet another embodiment, a fragment of PARIS-1 comprising a domain of the PARIS-1 protein is expressed.

Any of the methods previously described for the insertion of DNA fragments into a vector can be used to construct expression vectors containing a chimeric gene consisting of appropriate transcriptional/translational control signals and the protein coding sequences. These methods include in vitro recombinant DNA and synthetic techniques and in vivo recombinants (genetic recombination). Expression of nucleic acid sequence encoding a PARIS-1 protein or peptide fragment can be regulated by a second nucleic acid sequence so that the PARIS-1 protein or peptide is expressed in a host transformed with the recombinant DNA molecule. For example, expression of a PARIS-1 protein can be controlled by any promoter/enhancer element known in the art. Promoters which can be used to control PARIS-1 expression include, but are not limited to, the SV40 early promoter region (Bernoist and Chambon, *Nature* 290:304–310 (1981)), the promoter contained in the 3' long terminal repeat of Rous sarcoma virus (Yamamoto, et al., *Cell* 22:787–797 (1980)), the herpes thymidine kinase promoter (Wagner et al., *Proc. Natl. Acad. Sci. USA* 78:1441–1445 (1981)), the regulatory sequences of the metallothionein gene (Brinster et al., *Nature* 296:39–42 (1982)); prokaryotic expression vectors such as the (β-lactamase promoter (Villa-Kamaroff, et al., *Proc. Natl. Acad. Sci. USA* 75:3727–3731 (1978)), or the tac promoter (DeBoer, et al., *Proc. Natl. Acad. Sci. USA* 80:21–25 (1983)); plant expression vectors comprising the cauliflower mosaic virus 35S RNA promoter (Gardner, et al., *Nucl. Acids Res.* 9:2871 (1981)), and the promoter of the photosynthetic enzyme ribulose biphosphate carboxylase (Herrera-Estrella et al., *Nature* 310:115–120 (1984)); promoter elements from yeast or other fungi such as the Gal 4 promoter, the ADC (alcohol dehydrogenase) promoter, PGK (phosphoglycerol kinase) promoter, alkaline phosphatase promoter The following animal transcriptional control regions, which exhibit tissue specificity and have been utilized in transgenic animals: elastase I gene control region which is active in pancreatic acinar cells (Swift et al., *Cell* 38:639–646 (1984); Ornitz et al., *Cold Spring Harbor Symp. Quant. Biol.* 50:399–409 (1986); MacDonald, *Hepatology* 7:425–515 (1987); insulin gene control region which is active in pancreatic beta cells (Hanahan, 1985, *Nature* 315:115–122 (1985)), immunoglobulin gene control region which is active in lymphoid cells (Grosschedl et al., *Cell* 38:647–658 (1984); Adames et al., *Nature* 318:533–538 (1985); Alexander et al., *Mol. Cell. Biol.* 7:1436–1444 (1987)), mouse mammary tumor virus control region which is active in testicular, breast, lymphoid and mast cells (Leder et al., *Cell* 45:485–495 (1986)), albumin gene control region which is active in liver (Pinkert et al., *Genes Devel.* 1:268–276 (1987)), alpha-fetoprotein gene control region which is active in liver (Krumlauf et al., *Mol. Cell. Biol.* 5:1639–1648 (1985); Hammer et al., *Science* 235:53–58 (1987); alpha 1-antitrypsin gene control region which is active in the liver (Kelsey et al., *Genes Devel.* 1:161–171 (1987)), beta-globin gene control region which is active in myeloid cells (Mogram et al., *Nature* 315:338–340 (1985); Kollias et al., *Cell* 46:89–94 (1986); myelin basic protein gene control region which is active in oligodendrocyte cells in the brain (Readhead et al., *Cell* 48:703–712 (1987)); myosin light chain-2 gene control region which is active in skeletal muscle (Sani, *Nature* 314:283–286 (1985)), and gonadotropic releasing hormone gene control region which is active in the hypothalamus (Mason et al., *Science* 234: 1372–1378 (1986)).

In a specific embodiment, a vector is used that comprises a promoter operably linked to a PARIS-1-encoding nucleic acid, one or more origins of replication, and, optionally, one or more selectable markers (i.e., an antibiotic resistance gene). For example, an expression construct can be made by subcloning a PARIS-1 coding sequence into the EcoRI restriction site of each of the three pGEX vectors (Glutathione 5-Transferase expression vectors; Smith and Johnson, *Gene* 7:31–40 (1988)). This allows for the expression of the PARIS-1 protein product from the subclone in the correct reading frame.

Expression vectors containing PARIS-1 gene inserts can be identified by three general approaches well known to the skilled artisan, including: (a) nucleic acid hybridization, (b) presence or absence of "marker" gene function, and (c) expression of inserted sequences. In the first approach, the presence of a PARIS-1 gene inserted in an expression vector can be detected by nucleic acid hybridization using probes comprising sequences that are homologous to at least a portion of an inserted PARIS-1 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, and the like) caused by the insertion of a PARIS-1 gene in the vector. For example, if the PARIS-1 gene is inserted within the marker gene sequence of the vector, recombinants containing the PARIS-1 insert can be identified by the absence of the marker gene function.

In the third approach, recombinant expression vectors can be identified by assaying the PARIS-1 product expressed by the recombinant. Such assays can be based, for example, on the physical or functional properties of the PARIS-1 protein in in vitro assay systems, (i.e., binding with anti-PARIS-1 antibody, promotion of cell proliferation, and the like). Once a particular recombinant DNA molecule is identified and isolated, several methods known in the art can be used to propagate it. Once a suitable host system and growth conditions are established, recombinant expression vectors can be propagated and prepared in quantity. As previously explained, the expression vectors which can be used include, but are not limited to the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain can be chosen which modulates the expression of the inserted sequences, or modifies and processes the gene product in the specific fashion desired. Expression from certain promoters can be elevated in the presence of certain inducers; thus, expression of the genetically engineered PARIS-1 protein can be controlled. Furthermore, different host cells having characteristic and specific mechanisms for the translational and post-translational processing and modification (i.e., glycosylation, phosphorylation) of proteins can be used. Appropriate cell lines or host systems can be chosen to ensure the desired modification and processing of the foreign protein expressed. For example, expression in a bacterial system can be used to produce an unglycosylated core protein product. Expression in yeast will produce a glycosylated product.

Expression in mammalian cells can be used to ensure "native" glycosylation of a heterologous protein. Furthermore, different vector/host expression systems can effect processing reactions to different extents.

In other specific embodiments, the PARIS-1 protein, fragment, analog, or derivative can be expressed as a fusion, or chimeric protein product (comprising the protein, fragment, analog, or derivative joined via a peptide bond to a heterologous protein sequence (a different protein)). Such a chimeric product can be made by ligating the appropriate nucleic acid sequences encoding the desired amino acid sequences to each other by methods known in the art, in the proper coding frame, and expressing the chimeric product by methods commonly known to the skilled artisan. Alternatively, such a chimeric product can be made by protein synthetic techniques, (i.e., by use of a peptide synthesizer). Also, both cDNA and genomic sequences can be cloned and expressed.

Identification and Purification of the PARIS-1 Gene Products:

In particular aspects, the invention provides amino acid sequences of PARIS-1, preferably human PARIS-1 (SEQ ID NO: 4), and fragments and derivatives thereof which comprise an antigenic determinant (i.e., can be recognized by an antibody) or which are otherwise functionally active, as well as nucleic acid sequences encoding the foregoing. "Functionally active" PARIS-1 fragments and derivatives as used herein refers to those fragments and derivatives displaying one or more known functional activities associated with a full-length (wild-type) PARIS-1 protein, (i.e., inhibition of cell proliferation, binding to a PARIS-1 substrate or PARIS-1 binding partner, antigenicity (binding to an anti-PARIS-1 antibody), immunogenicity, and the like.

In specific embodiments, the invention provides fragments of a PARIS-1 protein consisting of at least 8 amino acids, 10 amino acids, 50 amino acids, or of at least 75 amino acids. Fragments, or proteins comprising fragments, lacking some or all of regions of a PARIS-1 protein are also provided. Nucleic acids encoding the foregoing are also provided and are considered part of the present invention.

Once a recombinant host cell which expresses the PARIS-1 gene sequence is identified, the gene product can be analyzed. This is achieved by assays based on the physical or functional properties of the product, including radioactive labeling of the product followed by analysis by gel electrophoresis, immunoassay, and the like. Once the PARIS-1 protein is identified, it can be isolated and purified by standard methods including chromatography (e.g., ion exchange, affinity, and sizing column chromatography), centrifugation, differential solubility, or by any other standard technique for the purification of proteins. The functional properties can be evaluated using any suitable assay as described herein. Alternatively, once a PARIS-1 protein produced by a recombinant is identified, the amino acid sequence of the protein can be deduced from the nucleotide sequence of the chimeric gene contained in the recombinant. As a result, the protein can be synthesized by standard chemical methods known in the art (See for example, Hunkapiller, M., et al., *Nature* 310:105–111 (1984); Stewart and Young, *Solid Phase Peptide Synthesis*, 2$^{nd}$ Edition, Pierce Chemical Company, Rockford, Ill., (1984)).

In another alternate embodiment, native PARIS-1 proteins can be purified from natural sources, by standard methods such as those described above (e.g., immunoaffinity purification). In a specific embodiment of the present invention, PARIS-1 proteins, whether produced by recombinant DNA techniques or by chemical synthetic methods, or by purification of native proteins, include but are not limited to those containing as a primary amino acid sequence all or part of the amino acid sequence of human PARIS-1 (SEQ ID NO: 4), as well as fragments, derivatives and analogs thereof.

Structure of the PARIS-1 Gene and Protein:

The structure of the PARIS-1 gene and protein can be analyzed by various methods known in the art. The cloned DNA or cDNA corresponding to the PARIS-1 gene can be analyzed by methods including but not limited to Southern hybridization (Southern, *J. Mol. Biol.* 98:503–517 (1975)), Northern hybridization (see for example Freeman et al., *Proc. Natl. Acad. Sci. USA* 80:4094–4098 (1983)), restriction endonuclease mapping (Sambrook et al., *Molecular Cloning, A Laboratory Manual*, 2d Ed., Cold Spring Harbor Laboratory Press, Cold Spring Harbor, N.Y. (1989)), and DNA sequence analysis. Polymerase chain reaction (PCR; see, for example, U.S. Pat. Nos. 4,683,202; 4,683,195 and 4,889,818; Gyllenstein et al., 1988, *Proc. Natl. Acad. Sci. USA* 85:7652–7656 (1988); Ochman et al., *Genetics* 120: 621–623 (1988); Loh et al., *Science* 243:217–220 (1989)) followed by Southern hybridization with a PARIS-1-specific probe can allow the detection of the PARIS-1 gene in DNA from various cell types. Methods of amplification other than PCR are commonly known and can also be employed.

In one embodiment, Southern blot hybridization can be used to determine the genetic linkage of PARIS-1. Northern blot hybridization analysis can be used to determine the expression of the PARIS-1 gene. Various cell types, at various states of development or activity can be tested for PARIS-1 expression. The stringency of the hybridization conditions for both Southern and Northern blot hybridization can be manipulated to ensure detection of nucleic acids with the desired degree of relatedness to the specific PARIS-1 probe used. Modifications of these methods and other methods commonly known in the art can be used. Restriction endonuclease mapping can be used to roughly determine the genetic structure of the PARIS-1 gene. Restriction maps derived by restriction endonuclease cleavage can be confirmed by DNA sequence analysis. DNA sequence analysis can be performed by any techniques known in the art, including, but not limited to, the method of Maxam and Gilbert (*Meth. Enzymol.* 65:499–560 (1980)), the Sanger dideoxy method (Sanger, et al., *Proc. Natl. Acad. Sci. USA* 74:5463–5467 (1977)), the use of T7 DNA polymerase (Tabor and Richardson, U.S. Pat. No. 4,795,699), or use of an automated DNA sequenator (e.g., Applied Biosystems, Foster City, Calif.).

The amino acid sequence of the PARIS-1 protein can be derived by deduction from the DNA sequence, or alternatively, by direct sequencing of the protein, e.g., with an automated amino acid sequencer. The PARIS-1 protein sequence can be further characterized by a hydrophilicity analysis (Hopp and Woods, *Proc. Natl. Acad. Sci. USA* 78:3824–3828 (1981)). A hydrophilicity profile can be used to identify the hydrophobic and hydrophilic regions of the PARIS-1 protein and the corresponding regions of the gene sequence which encode such regions.

Secondary, structural analysis (Chou and Fasman, *Biochemiistry* 13:222–245 (1974)) can also be done, to identify regions of PARIS-1 that assume specific secondary structures. Manipulation, translation, and secondary structure prediction, open reading frame prediction and plotting, as well as determination of sequence identity and similarities, can also be accomplished using computer software programs available in the art. Other methods of structural analysis can also be employed. These include, but are not limited to, X-ray crystallography (Engstom, *Biochem. Exp. Biol.* 11:7–13 (1974)) and computer modeling (Fletterick and Zoller (eds.), "Computer Graphics and Molecular Modeling", in, *Current Communications in Molecular Biology*, Cold Spring Harbor Laboratory, Cold Spring Harbor, N.Y. (1986)).

Generation of Antibodies to PARIS-1 Proteins, Derivatives and Analogs:

According to the invention, PARIS-1 protein, its fragments, derivatives, or analogs thereof, can be used as an immunogen to generate antibodies which immunospecifically bind PARIS-1. Such antibodies include, but are not limited to, polyclonal, monoclonal, chimeric, single chain, Fab fragments, a Fab expression library, and the like. In a specific embodiment, polyclonal and monoclonal antibodies to whole, intact human PARIS-1 protein are produced. In another embodiment, antibodies to a domain of a human PARIS-1 protein are produced. In a specific embodiment, fragments of a human PARIS-1 protein identified as hydrophilic are used as immunogens for antibody production.

Various procedures known in the art can be used for the production of polyclonal antibodies to a PARIS-1 protein, fragment, derivative or analog thereof. For the production of antibody, various host animals can be immunized by injection with the native PARIS-1 protein, or a synthetic version, or derivative (i.e., a fragment thereof), including but not limited to rabbits, mice, rats, and the like. Various adjuvants can be used to increase the immune response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a PARIS-1 protein, fragment, derivative, or analog thereof, any technique which provides for the production of antibody molecules by continuous cell lines in culture can be used. For example, the hybridoma technique originally developed by Kohler and Milstein (*Nature* 256:495–497 (1975)), as well as the trioma technique, the human B-cell hybridoma technique (Kozbor et al., *Immunology Today* 4:72 (1983)), and the EBV-hybridoma technique to produce human monoclonal antibodies (Cole et al., in *Monoclonal Antibodies and Cancer Therapy*, Alan R. Liss, Inc., pp. 77–96 (1985)). According to the invention, human antibodies may be used and can be obtained by using human hybridomas (Cote et al., *Proc. Natl. Acad. Sci. USA* 80:2026–2030 (1983)) or by transforming human B cells with EBV virus in vitro (Cole et al., in, *Monoclonal Antibodies and Cancer Therapy*, Alan R. Liss, pp. 77–96 (1985)). Further to the invention, techniques developed for the production of "chimeric antibodies" (Morrison, et al., *Proc. Natl. Acad. Sci. USA* 81:6851–6855 (1984); Neuberger, et al., *Nature* 312:604–608 (1984); Takeda, et al., *Nature* 314:452–454 (1985)) by splicing the genes from a vertebrate antibody molecule specific for PARIS-1 together with genes from a human antibody molecule of appropriate biological activity can be used; such antibodies are within the scope of this invention.

According to the invention, techniques described for the production of single chain antibodies (See, for example, U.S. Pat. Nos. 4,946,778 and 5,969,108) can be adapted to produce PARIS-1-specific single chain antibodies. An additional embodiment of the invention utilizes the techniques described for the construction of a Fab expression library (Ruse et al., *Science* 246:1275–1281 (1989)) to allow rapid and easy identification of monoclonal Fab fragments with the desired specificity for PARIS-1 proteins, fragments, derivatives, or analogs thereof.

Antibody fragments which contain the idiotype of the molecule can be generated by known techniques. For example, such fragments include but are not limited to; the $F(ab')_2$ fragment which can be produced by pepsin digestion of the antibody molecule; the Fab' fragments which can be generated by reducing the disulfide bridges of the $F(ab')_2$ fragment, the Fab fragments which can be generated by treating the antibody molecule with papain and a reducing agent, and Fv fragments. Also, recombinant Fv fragments can be produced in eukaryotic cells using, for example, the methods described in U.S. Pat. No. 5,965,405

In the production of antibodies, screening for the desired antibody can be accomplished by techniques known in the art, (e.g., ELISA (enzyme-linked immunosorbent assay). In one example, antibodies which recognize a specific domain of a PARIS-1 protein can be used to assay generated hybridomas for a product which binds to a PARIS-1 fragment containing the domain. For selection of an antibody that specifically binds a first PARIS-1 homolog but which does not specifically bind a different PARIS-1 homolog, one can select on the basis of antibody positive binding to the first PARIS-1 homolog and a lack of antibody binding to the second PARIS-1 homolog.

Antibodies specific to a domain of a PARIS-1 protein are also provided. The foregoing antibodies can be used in methods known in the art relating to the localization and activity of the PARIS-1 protein sequences of the invention, (i.e., for imaging proteins, measuring levels thereof in appropriate physiological samples, in diagnostic methods, and the like). In another embodiment of the invention (see infra), anti-PARIS-1 antibodies and fragments thereof containing the antigen binding domain are used as agents and compositions to slow or abate the growth of prostate tumor.

PARIS-1 Proteins, Derivatives and Analogs:

The invention further relates to PARIS-1 proteins, and derivatives (including, but not limited to, fragments) and analogs of PARIS-1 proteins. Nucleic acids encoding PARIS-1 protein derivatives and protein analogs are also provided. In one embodiment, the PARIS-1 proteins are encoded by the PARIS-1 nucleic acids described above. In particular aspects, the proteins, derivatives, or analogs are of PARIS-1 proteins of animals, (e.g., mouse, rat, pig, cow, dog, monkey, or human). The production and use of fragments, derivatives and analogs thereof related to PARIS-1 are within the scope of the present invention. In a specific embodiment, the fragment, derivative or analog is functionally active, (i.e., capable of exhibiting one or more functional activities associated with a full-length, wild-type PARIS-1 protein). As one example, such fragments, derivatives or analogs which have the desired immunogenicity or antigenicity can be used, for example, in immunoassays, for immunization, for inhibition of PARIS-1 activity, and the like. Fragments, derivatives or analogs that retain, or alternatively lack or inhibit, a desired PARIS-1 property of interest (i.e., binding to a PARIS-1 binding partner, promotion of cell proliferation), can be used as inducers, or inhibitors, respectively, of such property and its physiological correlates. A specific embodiment relates to a PARIS-1 fragment that can be bound by an anti-PARIS-1 antibody. Fragments, derivatives or analogs of PARIS-1 can be tested for the desired activity by procedures known in the art, including, but not limited to, the assays described herein.

In particular, PARIS-1 derivatives can be made by altering PARIS-1 sequences by substitutions, additions or deletions that provide for functionally equivalent molecules. Due to the degeneracy of nucleotide coding sequences, other DNA sequences which encode substantially the same amino acid sequence as a PARIS-1 gene, for example, the nucleic acid depicted as SEQ ID NO: 3, can be used in the practice of the present invention. These include, but are not limited to, nucleotide sequences comprising all or portions of a PARIS-1 gene which is altered by the substitution of different codons that encode a functionally equivalent amino acid residue within the sequence, thus producing a silent change. Likewise, the PARIS-1 derivatives of the invention include, but are not limited to, those containing as a primary amino acid sequence all or part of the amino acid sequence of a PARIS-1 protein including altered sequences in which functionally equivalent amino acid residues are substituted for residues within the sequence resulting in a silent change.

For example, one or more amino acid residues within the sequence can be substituted by another amino acid of a similar polarity which acts as a functional equivalent, resulting in a silent alteration. Substitutes for an amino acid within the sequence can be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a PARIS-1 protein consisting of at least 10 contiguous amino acids of the PARIS-1 protein is provided. In other embodiments, the fragment consists of at least 20 or 50 contiguous amino acids of the PARIS-1 protein. In a specific embodiment, the fragments are not larger than 35, 100 or even 200 amino acids. Fragments, derivatives or analogs of PARIS-1 include, but are not limited to, those molecules comprising regions that are substantially similar to PARIS-1 or fragments thereof (e.g., in various embodiments, at least 60% or 70%, or 80%, or 90% or up to 95% identity over an amino acid sequence of identical size), or when compared to an aligned sequence in which the alignment is done by a computer homology program known in the art) or whose encoding nucleic acid is capable of hybridizing to a PARIS-1 coding sequence, under stringent, moderately stringent, or nonstringent conditions.

The PARIS-1 derivatives and analogs of the invention can be produced by various methods known in the art. The manipulations which result in their production can occur at the gene or protein level. For example, the cloned PARIS-1 gene sequence can be modified by any of numerous strategies known in the art, (Sambrook et al., *Molecular Cloning, A Laboratory Manual*, 2d Ed., Cold Spring Harbor Laboratory Press, Cold Spring Harbor, N.Y. (1989)). The sequence can be cleaved at appropriate sites with restriction endonuclease(s), followed by further enzymatic modification if desired, isolated, and ligated in vitro. In the production of the gene encoding a fragment, derivative or analog of PARIS-1, care should be taken to ensure that the modified gene remains within the same translational reading frame as PARIS-1, uninterrupted by translational stop signals, in the gene region where the desired PARIS-1 activity is encoded. Additionally, the PARIS-1 encoding nucleic acid sequence can be mutated in vitro or in vivo, to create and/or destroy translation, initiation, and/or termination sequences. Also, the PARIS-1 encoding sequence can be mutated to create variations in coding regions and/or to form new restriction endonuclease sites or destroy preexisting ones, to facilitate further in vitro modification. Any technique for mutagenesis known in the art can be used, including, but not limited to, chemical mutagenesis, in vitro site-directed mutagenesis (Hutchinson et al., *J. Biol. Chem.* 253:6551 (1978)), use of TAB® linkers (Pharmacia), and the like.

Manipulations of the PARIS-1 sequence may also be made at the protein level. Included within the scope of the invention are PARIS-1 protein fragments or other derivatives or analogs which are differentially modified during or after translation, (i.e., by glycosylation, acetylation, phosphorylation, amidation, derivatization by known protecting/blocking groups, proteolytic cleavage, linkage to an antibody molecule or other cellular ligand, and the like). Any of numerous chemical modifications can be carried out by known techniques, including, but not limited to, specific chemical cleavage by cyanogen bromide; enzymatic cleavage by trypsin, chymotrypsin, papain, V8 protease, and the like, modification by, for example, $NaBH_4$ acetylation, formylation, oxidation, reduction; metabolic synthesis in the presence of tunicamycin; and the like.

In addition, fragments, derivatives and analogs of PARIS-1 can be chemically synthesized. For example, a peptide corresponding to a portion, or fragment, of a PARIS-1 protein which comprises a desired domain, or which mediates a desired activity in vitro, can be synthesized by use of a peptide synthesizer. Furthermore, if desired, nonclassical amino acids or chemical amino acid analogs can be introduced as a substitution or addition into the PARIS-1 amino acid sequence. Non-classical amino acids include but are not limited to the D-isomers of the common amino acids, (α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvalne, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

In a specific embodiment, the PARIS-1 fragment or derivative is a chimeric, or fusion, protein comprising a PARIS-1 protein or fragment thereof (typically consisting of at least a domain or motif of the PARIS-1 protein, or at least 10 contiguous amino acids of the PARIS-1 protein) joined at its amino- or carboxy-terminus via a peptide bond to an amino acid sequence of a different protein. In one embodiment, such a chimeric protein is produced by recombinant expression of a nucleic acid encoding the protein. The chimeric product can be made by ligating the appropriate nucleic acid sequence encoding the desired amino acid sequences to each other by methods known in the art, in the proper coding frame, and expressing the chimeric product by methods commonly known in the art. Alternatively, the chimeric product can be made by protein synthetic techniques, (e.g., by use of a peptide synthesizer).

In another specific embodiment, the PARIS-1 derivative is a molecule comprising a region of "similarity" with a human PARIS-1 protein. By way of example, in various embodiments, a first protein region can be considered similar to a region of human PARIS-1 when the amino acid sequence of the first region is at least 30%, 40%, 50%, 60%, 70%, 75%, 80%, 90%, or even 95% identical to a region of PARIS-1 when compared to any sequence in PARIS-1 of an equal number of amino acids as the number contained in the first region, or when compared to an aligned sequence of human PARIS-1 that has been aligned by a computer similarity program known in the art.

Optimal alignment of sequences for comparison can be conducted, e.g., by the local homology algorithm of Smith et al., *Adv. Appl. Math.* 2:482 (1981), by the homology alignment algorithm of Needleman et al., *J. Mol. Biol.* 48:443–453 (1970), by the search for similarity method of Pearson et al., *Proc. Natl. Acad. Sci. USA* 85:2444–2448 (1988), by computerized implementations of these algorithms (GAP, BESTFIT, FASTA, and TFASTA in the Wisconsin Genetics Software Package, Genetics Computer Group, 575 Science Drive, Madison, Wis.), or by visual inspection).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng et al. *J. Mol. Evol.* 35:351–360 (1987). The method used is similar to the method described by Higgins et al., *CABIOS* 5:151–153 (1989). The program can align up to 300 sequences, each of a maximum length of 5,000 nucleotides or amino acids. The multiple alignment procedure begins with the pairwise alignment of the two most related sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their nucleotide or amino acid coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as for as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and the speed of the alignment. The BLAST program uses as defaults a wordlength (W) of 11, the BLOSUM62 scoring matrix (see, Henikoff et al., *Proc. Natl. Acad. Sci. USA* 89:10915–10919 (1992)) alignments (B) of 50, expectation (E) of 10, M=5, N=−4, and a comparison of both strands.

In addition to calculating percent sequence identity, the BLAST algorithm also performs statistical analysis of the similarity between two sequences (see e.g., Karlin et al., *Proc. Natl. Acad. Sci. USA* 90:5873–5877 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison test is less than about 0.1, more preferably less than about 0.01, and most preferably less than about 0.001. Additional methods and algorithms for sequence alignment and analysis of sequence similarity are well known to the skilled artisan.

Assays for Activity of PARIS-1 Proteins, Fragments, Derivatives, and Analogs:

The functional activity of PARIS-1 proteins, fragments, derivatives and analogs can be assayed by various methods. For example, in one embodiment, where assaying for the ability to bind or compete with wild-type PARIS-1 for binding to anti-PARIS-1 antibody, various immunoassays known in the art can be used, including but not limited to competitive and non-competitive assay systems using techniques such as radioimmunoassays, ELISA (enzyme linked immunosorbent assay) "sandwich" immunoassays, immunoradiometric assays, gel diffusion precipitin reactions, immunodiffusion assays, in situ immunoassays (using colloidal gold, enzyme or radioisotope labels, and the like), Western blots, precipitation reactions, agglutination assays (e.g., gel agglutination assays, hemagglutination assays), complement fixation assays, immunofluorescence assays, protein A assays, and immunoelectrophoresis assays, and the like. In one embodiment, antibody binding is detected by measuring a label on the primary antibody. Alternatively, the primary antibody is detected by measuring binding of a secondary antibody or reagent to the primary antibody. The secondary antibody can also be directly labeled. Many means are known in the art for detecting binding in an immunoassay and are considered within the scope of the present invention.

In another embodiment, a PARIS-1-binding protein is identified by detection of binding with PARIS-1 by means well known in the art. In yet another embodiment, physiological changes in cells or tissues can be measured and correlate with PARIS-1 binding to its substrates (for example, signal transduction). In addition, assays that can be used to detect or measure the ability to inhibit, or alternatively promote, cell proliferation can be used to identify PARIS-1 binding agents.

In Vivo Uses of PARIS-1 Nucleic Acids and PARIS-1 Protein:

The invention provides further for methods for the administration of an agent or compound which can modulate the effects of PARIS-1 on cell proliferation. Agents and compounds of the invention include, but are not limited to, PARIS-1 proteins, fragments, derivatives and analogs thereof as described hereinabove; antibodies specific for PARIS-1, fragments, derivatives and analogs thereof (as described hereinabove); nucleic acids encoding PARIS-1 protein, fragments, derivatives and analogs thereof (as described hereinabove); PARIS-1 antisense nucleic acids, and PARIS-1 agonists and antagonists. Disorders involving tumorigenesis or cell overproliferation require the use of a method for administration of an agent or compound that promotes PARIS-1 function. While disorders in which cell proliferation is deficient or is desired require the administration of an agent or compound that inhibits PARIS-1 function.

Generally, it is typical to administer a biological agent or compound of a species origin or species reactivity (in the case of antibodies) that is the same as that of the recipient. Thus, a human PARIS-1 protein, fragment, derivative, or analog thereof, or nucleic acid, or an antibody to a human PARIS-1 protein, is administered in a dose which is therapeutically or prophylactically effective.

Treatment and Prevention of Disorders Involving Overproliferation of Cells:

Diseases and disorders involving cell overproliferation are treated or prevented by administration of an agent that promotes PARIS-1 function. Examples of such an agent include but are not limited to nucleic acids encoding PARIS-1 under the control of a strong inducible promoter, particularly that are active in inhibiting cell proliferation. Other agents that can be used to promote PARIS-1 activity, can be identified using in vitro assays or animal models, examples of which are described infra.

In certain specific embodiments, agents that promote PARIS-1 function are administered therapeutically (including prophylactically) in diseases or disorders involving a decreased (relative to normal or desired) level of PARIS-1 protein or function. For example, the agent can be administered to a patient where PARIS-1 protein is underexpressed, genetically defective, or biologically hypoactive. Further, an agent of the invention can be administered in diseases or disorders wherein in vitro (or in vivo) assays indicate the utility of PARIS-1 agonist administration.

A decreased level in PARIS-1 protein or function can be readily detected, for example, by obtaining a patient tissue sample (such as from a biopsy tissue) and assaying the sample in vitro for RNA or protein levels, structure and/or activity of the expressed PARIS-1 RNA or PARIS-1 protein. Many methods standard in the art can be thus employed, including, but not limited to, immunoassays to detect and/or visualize PARIS-1 protein (i.e., Western blot, immunoprecipitation followed by sodium dodecyl sulfate polyacrylamide gel electrophoresis, immunocytochemistry, and the like) and/or hybridization assays to detect PARIS-1 expression by detecting and/or visualizing PARIS-1 mRNA (e.g., Northern blot assays, dot blots, in situ hybridization, and the like), among others known to the skilled artisan.

Diseases and disorders involving cell overproliferation that can be treated or prevented include but are not limited to malignancies, premalignant conditions (i.e., hyperplasia, metaplasia, dysplasia), benign tumors, hyperproliferative disorders, benign dysproliferative disorders, and the like. Examples of these include, but are not limited to prostate cancer and prostate hyperplasia. In another specific embodiment, an agent of the invention is administered to a human patient to prevent progression to prostate cancer.

Gene Therapy:

In a specific embodiment, anti-sense nucleic acids complementary to a sequence encoding a PARIS-1 protein, fragment, derivative or analog thereof, are administered to inhibit PARIS-1 function, by way of gene therapy. Gene therapy refers to therapy performed by the administration of a nucleic acid to a subject. In this embodiment of the invention, the antisense nucleic acid mediates a therapeutic effect by inhibiting PARIS-1 transcription and translation. Any of the methods for gene therapy available in the art can be used according to the present invention. Exemplary methods are described below.

For general reviews of the methods of gene therapy, see Goldspiel et al., *Clinical Pharmacy* 12:488–505 (1993); Wu and Wu, *Biotherapy* 3:87–95 (1991); Tolstoshev, *Ann. Rev. Pharmacol. Toxicol.* 32:573–596 (1993); Mulligan, *Science* 260:926–932 (1993); and Morgan and Anderson, *Ann. Rev. Biochem.* 62:191–217 (1993); May, *TIBTECH* 11:155–215 (1993)).

Methods commonly known in the art of recombinant DNA technology which can be used are described in Ausubel et al. (eds.), *Current Protocols in Molecular Biology*, John Wiley & Sons, NY (1993); and Kriegler, *Gene Transfer and Expression, A Laboratory Manual*, Stockton Press, NY (1990). In one embodiment, the agent comprises a PARIS-1 sense or antisense nucleic acid that is part of an expression vector that expresses a PARIS-1 protein or fragment or chimeric protein thereof in a suitable host. In particular, such a nucleic acid has a promoter operably linked to the PARIS-1 coding region, the promoter being inducible or constitutive, and, optionally, tissue-specific.

In another particular embodiment, a nucleic acid molecule is used in which the PARIS-1 coding sequences and any other desired sequences are flanked by regions that promote homologous recombination at a desired site in the genome, thus providing for intrachromosomal expression of the PARIS-1 nucleic acid (Koller and Smithies, *Proc. Natl. Acad. Sci. USA* 86:8932–8935 (1989); Zijlstra et al., *Nature* 342:435–438 (1989)). Delivery of the nucleic acid into a patient can be either direct, in which case the patient is directly exposed to the nucleic acid or nucleic acid-carrying vector, or indirect, in which case, cells are first transformed with the nucleic acid in vitro, then transplanted into the patient.

These two approaches are known, respectively, as in vivo or ex vivo gene therapy. In a specific embodiment, the nucleic acid is directly administered in vivo, where it is expressed to produce the encoded product. This can be accomplished by any of numerous methods known in the art, (i.e., by constructing it as part of an appropriate nucleic acid expression vector and administering it so that it becomes intracellular, for example, by infection using a defective or attenuated retroviral or other viral vector (see for example, U.S. Pat. No. 4,980,286), or by direct injection of naked DNA, or by use of microparticle bombardment, such as a gene gun; BIOLISTIC, Dupont). DNA can also be inserted into cells by coating naked DNA with lipids or cell-surface receptors or transfecting agents, encapsulation in liposomes, microparticles, or microcapsules, or by administering the DNA in linkage to a peptide which is known to enter the nucleus, by administering the DNA in linkage to a ligand subject to receptor-mediated endocytosis (see e.g., Wu and Wu, *J. Biol. Chem.* 262:4429–4432 (1987)) (which can be used to target cell types specifically expressing the receptors), and the like. In another embodiment, a nucleic acid-ligand complex can be formed in which the ligand comprises a fusogenic viral peptide to disrupt endosomes, allowing the nucleic acid to avoid lysosomal degradation.

In yet another embodiment, the nucleic acid can be targeted in vivo for cell specific uptake and expression, by targeting a specific receptor (see, e.g., WO 92/06180; WO 92/22635; WO92/20316; WO93/14188, WO 93/20221). Alternatively, the nucleic acid can be introduced intracellularly and incorporated within host cell DNA for expression, for example, by homologous recombination (Koller and Smithies, *Proc. Natl. Acad. Sci. USA* 86:8932–8935 (1989); Zijlstra et al., *Nature* 342:435–438 (1989)).

In a specific embodiment, a viral vector that contains the PARIS-1 nucleic acid is used. A retroviral vector, for example, can be used (see Miller et al., *Meth. Enzymol.* 17:581–599 (1993)). These retroviral vectors typically have been modified to delete retroviral sequences that are not necessary for packaging of the viral genome and integration into host cell DNA. The PARIS-1 nucleic acid to be used in gene therapy is cloned into the vector, which facilitates delivery of the gene into a patient. More detail about retroviral vectors can be found in, for example, Boesen et al. (*Biotherapy* 6:291–302(1994)), which describes the use of a retroviral vector to deliver the mdrl gene to hematopoietic stem cells in order to make the stem cells more resistant to chemotherapy. Other references illustrating the use of retroviral vectors in gene therapy include, for example: Clowes et al., *J. Clin. Invest.* 93:644–651 (1994); Kiem et al., *Blood* 83:1467–1473 (1994); Salmons and Gunzberg, *Human Gene Therapy* 4:129–141 (1993); and Grossman and Wilson, *Curr. Opin. in Genet. Devel.* 3:110–114 (1993).

Adenoviruses can also be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are prostate, liver, the central nervous system, endothelial cells, and muscle. Adenoviruses have the advantage of being capable of infecting non-dividing cells. Kozarsky and Wilson, (*Curr. Op. Genet. Dev.* 3:499–503 (1993)) present a review of adenovirus-based gene therapy. Bout et al., (*Human Gene Therapy* 5:3–10 (1994)) demonstrated the use of adenovirus vectors to transfer genes to the respiratory epithelia of rhesus monkeys. Herman et al., (*Human Gene Therapy* 10:1239–1249 (1999)), describe the intraprostatic injection of a replication-deficient adenovirus containing the herpes simplex thymidine kinase gene into human prostate, followed by intravenous administration of the prodrug ganciclovir in a phase I clinical trial. Other instances of the use of adenoviruses in gene therapy can be found in Rosenfeld et al., *Science* 252:431–434 (1991); Rosenfeld et al., *Cell* 68:143–155 (1992); Mastrangeli et al., *J. Clin. Invest.* 91:225–234 (1993); and Thompson, *Oncol. Res* 11:1–8 (1999), to list but a few.

Adeno-associated virus (AAV) has also been proposed for use in gene therapy (Walsh et al., *Proc. Soc. Exp. Biol. Med.* 204:289–300 (1993); Grimm et al., *Human Gene Therapy* 10:2445–2450(1999). Another approach to gene therapy involves transferring a gene to cells in tissue culture by methods such as electroporation, lipofection, calcium phosphate mediated transfection, or viral infection. Typically, the method of transfer includes the transfer of a selectable marker to the cells. The cells are then placed under culture conditions conducive to selection so as to isolate those cells that have taken up and are expressing the transferred gene. The cells selected are then delivered to a patient.

In one embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, and the like. Numerous techniques are known in the art for the introduction of foreign genes into cells (see for example, Loeffler and Behr, *Meth. Enzymol.* 217:599–618 (1993); Cohen et al., *Meth. Enzymol.* 217:618–644 (1993); Cline, *Pharmac. Ther.* 29:69–92 (1985)) and can be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Typically, cells are injected, for example, subcutaneously. In another embodiment, recombinant skin cells can be applied as a skin graft onto the patient. Recombinant blood cells (i.e., hematopoietic stem or progenitor cells) are typically administered intravenously. The amount of cells envisioned for use depends on the desired effect, state of the patients condition, and the like, and can be determined by one skilled in the art.

Cells into which a nucleic acid can be introduced for purposes of gene therapy encompass any desired available cell type, and include, but are not limited to, prostate cells, epithelial cells, endothelial cells, keratinocytes, fibroblasts, muscle cells, hepatocytes, blood cells, (such as T lymphocytes, B lymphocytes, monocytes, macrophages, neutrophils, eosinophils, megakaryocytes, granulocytes), various stem or progenitor cells, in particular, hematopoietic stem or progenitor cells, (i.e., as obtained from bone marrow, umbilical cord blood, peripheral blood, fetal liver, and the like). The cell used for gene therapy generally is autologous to the patient, but heterologous cells which can be typed for compatibility with the patient can be used.

Treatment and Prevention of Hyperproliferative and Dysproliferative Disorders:

Diseases and disorders involving an increase in cell proliferation (growth) or in which cell proliferation is otherwise undesirable, are treated or prevented by administration of an agent or composition that antagonizes (inhibits) PARIS-1 function. Agents that can be used include but are not limited to anti-PARIS-1 antibodies (and fragments and derivatives thereof containing the antigen binding region thereof), PARIS-1 antisense nucleic acids, and PARIS-1 nucleic acids that are dysfunctional (i.e., due to a heterologous (non-PARIS-1 sequence) insertion within the PARIS-1 coding sequence) that are used to "knockout" endogenous PARIS-1 function by homologous recombination (see, for example, Capecchi, *Science* 244:1288–1292 (1989)). In a specific embodiment of the invention, a nucleic acid containing a portion of a PARIS-1 gene, in which the PARIS-1 sequences flank both 5' and 3' a different gene sequence, is used to disrupt the expression of PARIS-1 by homologous recombination (see also Koller and Smithies, *Proc. Natl. Acad. Sci. USA* 86:8932–8935 (1989); Zijlstra et al., *Nature* 342:435–438 (1989)).

Other agents or compounds that inhibit PARIS-1 function can be identified by use of known convenient in vitro assays, (i.e., based on their ability to inhibit binding of PARIS-1 to another protein or to inhibit any known PARIS-1 function, as preferably assayed in vitro or in cell culture) can also be employed. Typically, suitable in vitro or in vivo assays are utilized to determine the effect of a specific agent and whether its administration is indicated for treatment of the affected tissue.

In specific embodiments, agents that inhibit PARIS-1 function are administered therapeutically (including prophylactically): (1) in diseases or disorders involving an increased (relative to normal or desired) level of PARIS-1 protein or function, for example, in patients where PARIS-1 protein is overactive or overexpressed; or (2) in diseases or disorders wherein in vitro (or in vivo) assays (see infra) indicate the utility of PARIS-1 antagonist administration. The increased levels in PARIS-1 protein or function can be readily detected, for example, by quantifying protein and/or RNA. Quantification can be accomplished by obtaining a patient tissue sample (e.g., from biopsy tissue) and assaying it in vitro for RNA or protein levels, structure and/or activity of the expressed PARIS-1 RNA or PARIS-1 protein. Many methods standard in the art can be employed, including, but not limited to, immunoassays to detect and/or visualize PARIS-1 protein (for example, Western blot, immunoprecipitation followed by sodium dodecyl sulfate polyacrylamide gel electrophoresis, immunocytochemistry, and the like) and/or hybridization assays to detect PARIS-1 expression by detecting and/or visualizing respectively PARIS-1 mRNA (for example, Northern blot assays, dot blots, in situ hybridization, and the like). In other embodiments, chemical mutagenesis, or homologous recombination with an insertionally inactivated PARIS-1 gene (see Capecchi, *Science* 244:1288–1292 (1989)) can be carried out to reduce or destroy endogenous PARIS-1 function, thereby increasing cell proliferation. Suitable methods, modes of administration and compositions, that can be used to inhibit PARIS-1 function are described herein.

Antisense Regulation of PARIS-1 Expression:

In a specific embodiment, PARIS-1 function is inhibited by use of PARIS-1 antisense nucleic acids. The present invention provides for the administration of nucleic acids of at least six nucleotides that are antisense to a gene or cDNA encoding PARIS-1 or a portion thereof to inhibit the function of PARIS-1. A PARIS-1 "antisense" nucleic acid as used herein refers to a nucleic acid which hybridizes to a portion of a PARIS-1 RNA (preferably mRNA) by virtue of some sequence complementarity. The antisense nucleic acid may be complementary to a coding and/or noncoding region of a PARIS-1 mRNA. Such antisense nucleic acids have utility as agents that inhibit PARIS-1 function, and can be used in the treatment or prevention of disorders as described infra.

The antisense nucleic acids of the invention can be oligonucleotides that are double-stranded or single-stranded, RNA or DNA, or a modification or derivative thereof, which can be directly administered to a cell, or which can be produced intracellularly by transcription of exogenous, introduced nucleic acid sequences.

In a specific embodiment, the PARIS-1 antisense nucleic acid provided by the instant invention can be used to prevent tumor or other forms of aberrant cell proliferation. The invention further provides pharmaceutical compositions comprising an effective amount of the PARIS-1 antisense nucleic acids of the invention in a pharmaceutically acceptable carrier, as described infra. In another embodiment, the invention is directed to methods for inhibiting the expression of a PARIS-1 nucleic acid sequence in a prokaryotic or eukaryotic cell comprising providing the cell with an effective amount of a composition comprising a PARIS-1 antisense nucleic acid of the invention. PARIS-1 antisense nucleic acids and their uses are described in detail below.

PARIS-1 Antisense Nucleic Acids:

The PARIS-1 antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or can be at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide can include other appending groups such as peptides, or agents facilitating transport across the cell membrane (see, for example, Letsinger et al., *Proc. Natl. Acad. Sci. USA* 86:6553–6556 (1989); Lemaitre et al., *Proc. Natl. Acad. Sci. USA* 84:648–652 (1987); WO 88/09810) or blood-brain barrier (see, e.g., WO 89/10134) hybridization-triggered cleavage agents (see, e.g., Krol et al., *BioTechniques* 6:958–976 (1988)) or intercalating agents (see, for example, Zon, *Pharm. Res.* 5:539–549 (1988)).

In one embodiment of the invention, a PARIS-1 antisense oligonucleotide is provided, typically of single-stranded DNA. The oligonucleotide can be modified at any position on its structure with substituents generally known in the art. The PARIS-1 antisense oligonucleotide can comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxy-hydroxylmethyl) uracil, 5-carboxymethylaminomethyl -2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, 2,6-diaminopurine, and the like.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625–6641 (1987)). The oligonucleotide can be conjugated to another molecule, (i.e., a peptide, hybridization triggered cross-linking agent, transport agent, hybridization-triggered cleavage agent, and the like).

Oligonucleotides of the invention can be synthesized by standard methods known in the art, (e.g., by use of a commercially available automated DNA synthesizer). As examples, phosphorothioate oligonucleotides can be synthesized by the method of Stein et al. (*Nucl. Acids Res.* 16:3209–3221 (1988)), methyphosphonate oligonucleotides can be prepared by use of controlled pore glass polymer supports (Sarin et al., *Proc. Natl. Acad. Sci. USA* 85:7448–7451 (1988)), and the like.

In a specific embodiment, the PARIS-1 antisense oligonucleotide comprises catalytic RNA, or a ribozyme (see, e.g., WO 90/11364; Sarver et al., *Science* 247:1222–1225 (1990)). In another embodiment, the oligonucleotide is a 2'-0-methyribonucleotide (Inoue et al., *Nucl. Acids Res.* 15:6131–6148 (1987)), or a chimeric RNA-DNA analogue (Inoue et al., *FEBS Lett.* 215:327–330 (1987)).

In an alternative embodiment, the PARIS-1 antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. The vector would contain a sequence encoding the PARIS-1 antisense nucleic acid. Once inside the cell the vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the PARIS-1 antisense RNA can be controlled by any promoter known in the art to act in mammalian, typically human, cells. The promoters can be inducible or constitutive. Inducible promoters include but are not limited to, the SV40 early promoter region (Bernoist and Chambon, *Nature* 290:304–310 (1981)), the promoter contained in the 3' long terminal repeat of Rous sarcoma virus (Yamamoto et al., *Cell* 22:787–797(1980)), the herpes thymidine kinase promoter (Wagner et al., *Proc. Natl. Acad. Sci. USA* 78:1441–1445(1981)), the regulatory sequences of the metallothionein gene (Brinster et al., *Nature* 296:39–42(1982)), and the like.

The antisense nucleic acids of the invention comprise a sequence complementary to at least a portion of an RNA transcript of a PARIS-1 gene, specifically a human PARIS-1 gene. However, absolute complementarity, although typical, is not required. A sequence "complementary to at least a portion of an RNA," as referred to herein, means a sequence having sufficient complementarity to be able to hybridize with the RNA, forming a stable duplex. In the case of double-stranded PARIS-1 antisense nucleic acids, a single strand of the duplex DNA can be tested, or triplex formation can be assayed. The ability to hybridize will depend on both the degree of complementarity and the length of the antisense nucleic acid. Generally, the longer the hybridizing nucleic acid, the more base mismatches with a PARIS-1 RNA it can contain and still form a stable duplex (or triplex, as the case may be). One skilled in the art can ascertain a tolerable degree of mismatch by use of standard procedures to determine the melting point of the hybridized complex.

Use of PARIS-1 Antisense Nucleic Acids as a PARIS-1 Modulating Agent or Composition:

The PARIS-1 antisense nucleic acids can be administered to an individual to treat (or prevent) disorders of a cell type that expresses, or more typically overexpresses, PARIS-1. In a specific embodiment, such a disorder is a growth deficiency. In one embodiment, a single-stranded DNA antisense PARIS-1 oligonucleotide is used. Cell types which express or overexpress PARIS-1 RNA can be identified by various methods known in the art. Such methods include, but are not limited to, hybridization with a PARIS-1-specific nucleic acid (i.e., by Northern blot hybridization, dot blot hybridization, in situ hybridization), observing the ability of RNA from the cell type to be translated in vitro into PARIS-1, immunoassay, and the like. In a typical example, primary tissue from a patient can be assayed for PARIS-1 mRNA expression prior to treatment, for example, by immunocytochemistry or in situ hybridization.

Compositions of the invention, comprising an effective amount of a PARIS-1 antisense nucleic acid in a pharmaceutically acceptable carrier, can be administered to a patient having a disease or disorder which is of a type that expresses or overexpresses PARIS-1 RNA or protein. The amount of PARIS-1 antisense nucleic acid which will be effective in the treatment of a particular disorder or condition will depend on the nature of the disorder or condition, and can be determined by standard clinical techniques. Where possible, it is typical to determine the antisense cytotoxicity of the tumor type to be treated in vitro, and then in useful animal model systems prior to testing and use in humans.

In a specific embodiment, compositions comprising PARIS-1 antisense nucleic acids and a pharmaceutically acceptable carrier are administered via liposomes, microparticles, or microcapsules. In various embodiments of the invention, it can be useful to use such compositions to achieve sustained release of the PARIS-1 antisense nucleic acids. In a specific embodiment liposomes targeted via antibodies to specific identifiable tumor antigens (Leonetti et al., *Proc. Natl. Acad. Sci. U.S.A.* 87:2448–2451 (1990); Renneisen et al., *J. Biol. Chem.* 265:16337–16342 (1990)) are utilized.

Treatment and Prevention of Hypoproliferative Disorders:

Diseases and disorders involving decreased cell proliferation or in which cell proliferation is desired for treatment or prevention, and that can be treated or prevented by inhibiting PARIS-1 tumor suppressor function, include, but are not limited to, degenerative disorders, growth deficiencies, hypoproliferative disorders, physical trauma, lesions, and wounds (for example, to promote wound healing, or to promote regeneration in degenerated, lesioned or injured tissues) and the like.

Administration of Agents and Compositions:

The invention provides methods for the administration to a subject an effective amount of an agent or composition of the invention. Typically, the agent is substantially purified prior to formulation. The subject can be an animal, including but not limited to, cows, pigs, horses, chickens, cats, dogs, and the like, and is typically a mammal, and in a particular embodiment human. In another specific embodiment, a non-human mammal is the subject.

Formulations and methods of administration that can be employed when the agent comprises a nucleic acid are described above; additional appropriate formulations and routes of administration can be selected from among those described hereinbelow.

Various delivery systems are known and can be used to administer an agent of the invention, e.g. encapsulation in liposomes, microparticles, microcapsules, recombinant cells capable of expressing the agent, receptor-mediated endocytosis (see, e.g. Wu and Wu, *J. Biol. Chem.* 262:4429–4432 (1987)), construction of an agent comprising a nucleic acid as part of a retroviral or other vector, and the like. Methods of introduction include but are not limited to intradermal, intramuscular, intraperitoneal, intravenous, subcutaneous, intranasal, epidural and oral routes. The compounds can be administered by any convenient route, for example, by infusion or bolus injection, by absorption through epithelial or mucocutaneous linings (e.g., oral mucosa, rectal and intestinal mucosa, and the like) and can be administered together with other biologically active agents. Administration can be systemic or local. In addition, it can be desirable to introduce the pharmaceutical composition comprising an agent or composition of the invention into the prostate by any suitable route, including intravenous and intrathecal injection. Pulmonary administration can also be employed, e.g., by use of an inhaler or nebulizer, and formulation of the agent with an aerosolizing agent.

In a specific embodiment, it can be desirable to administer the pharmaceutical compositions of the invention locally to the area in need of treatment; this can be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue, for example, a prostate tumor or the prostate gland.

In another embodiment, the agent can be delivered in a vesicle, in particular a liposome (see Langer, *Science* 249: 1527–1533 (1990); Treat et al., in, *Liposomes in the Therapy of Infectious Disease and Cancer*, Lopez-Berestein and Fidler (eds.), Liss, New York, pp. 353–365 (1989); Lopez-Berestein, *ibid.*, pp. 317–327).

In yet another embodiment, the agent can be delivered in a controlled release system. In one embodiment, a pump can be used (see Langer, supra; Sefton, *Crit. Rev. Biomed. Eng.* 14:201–240 (1987); Buchwald et al., *Surgery* 88:507–516 (1980); Saudek et al., *N. Engl. J. Med.* 321:574–579 (1989)). In another embodiment, polymeric materials can be used (see *Medical Applications of Controlled Release*, Langer and Wise (eds.), CRC Press, Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.* 23:61 (1983); see also Levy et al., *Science* 228:190–192 (1985); During et al., *Ann. Neurol.* 25:351–356 (1989); Howard et al., *J. Neurosurg.* 71:105 (1989)). In yet another embodiment, a controlled release system can be placed in proximity of the therapeutic target, i.e., the prostate, thus requiring only a fraction of the systemic dose (see, e.g., Goodson, in *Medical Applications of Controlled Release*, supra, Vol. 2, pp. 115–138 (1984)). Other controlled release systems are discussed in, for example, the review by Langer (*Science* 249:1527–1533 (1990)).

Where the agent is a nucleic acid encoding a protein, the nucleic acid can be administered in vivo to promote expression of its encoded protein, by constructing it as part of an appropriate nucleic acid expression vector and administering it so that it becomes intracellular, for example, by use of a retroviral vector (see U.S. Pat. No. 4,980,286), or by direct injection, or by use of microparticle bombardment (e.g., a gene gun; BIOLISTIC, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA* 88:1864–1868 (1991)), and the like. Alternatively, an agent which comprises a nucleic acid can be introduced intracellularly and incorporated within host cell DNA for expression, by homologous recombination as described above.

The present invention also provides pharmaceutical compositions. Such compositions comprise a therapeutically effective amount of an agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more typically in humans. The term "carrier" refers to a diluent, adjuvant, excipient, or vehicle with which the agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Water is a typical carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Pharmaceutical compositions can take the form of solutions, suspensions, emulsion, tablets, pills, capsules, powders, sustained-release formulations, and the like. The composition can be formulated as a suppository, with traditional binders and carriers such as triglycerides.

Oral formulations can include standard carriers such as pharmaceutical grades of mannitol, lactose, starch, magnesium stearate, sodium saccharine, cellulose, magnesium carbonate, and the like. Examples of suitable pharmaceutical carriers are described in, for example, *Remington's Pharmaceutical Sciences*, by E. W. Martin. Such compositions will contain a therapeutically effective amount of the agent of the present invention, preferably in purified form, together with a suitable amount of carrier so as to provide a formulation proper for administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form. For example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The agents of the invention can be formulated as neutral or salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

The amount of the agent of the invention which will be effective in the treatment of a particular disorder or condition as indicated by modulation of cell proliferation will depend on the nature of the disorder or condition, and can be determined by standard clinical techniques. In addition, in vitro assays can optionally be employed to help identify optimal dosage ranges. The precise dose of the agent to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active agent per kilogram body weight. Suitable dosage ranges for intranasal administration are generally about 0.01 pg/kg body weight to 1 mg/kg body weight. Effective doses can be extrapolated from dose response curves derived from in vitro or animal model test systems. Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Agents which are useful according to this embodiment of the invention for treatment of a disorder can be selected by testing for biological activity in promoting the survival or differentiation of cells.

Diagnosis and Screening:

PARIS-1 proteins, fragments, derivatives, and analogs thereof, PARIS-1 nucleic acids (and sequences complementary thereto), anti-PARIS-1 antibodies, also have utility in diagnostics. Such molecules can be used in assays, such as immunoassays, to detect, prognose, diagnose, or monitor various conditions, diseases, and disorders affecting PARIS-1 expression, or to monitor the treatment thereof. In particular, methods, such an immunoassay, can be carried out by steps comprising contacting a sample derived from a patient with an anti-PARIS-1 antibody under conditions such that immunospecific binding can occur, and detecting or measuring the amount of any immunospecific binding by the antibody. In a specific aspect, binding of antibody to PARIS-1, in tissue sections, can be used to detect aberrant PARIS-1 localization or aberrant, e.g., low or absent) levels of PARIS-1. In a specific embodiment, antibody to PARIS-1 can be used to assay a patient tissue or serum sample for the presence of PARIS-1 where an aberrant level of PARIS-1 is an indication of a diseased condition. By "aberrant levels," is meant increased or decreased levels relative to that present, or a standard level representing that present, in an analogous sample from a portion of the body or from a subject not having the disorder.

The immunoassays which can be used include, but are not limited to, competitive and non-competitive assay systems using techniques such as Western blot, radioimmunoassay, ELISA (enzyme linked immunosorbent assay), "sandwich" immunoassay, immunoprecipitation assay, precipitin reaction, gel diffusion precipitin reaction, immunodiffusion assay, agglutination assay, complement-fixation assay, immunoradiometric assay, fluorescent immunoassay, protein A immunoassay, to name but a few.

PARIS-1 genes and related nucleic acid sequences and subsequences, including complementary sequences, can also be used in hybridization assays. PARIS-1 nucleic acid sequences (SEQ ID NO:3), or subsequences thereof comprising about at least 8 nucleotides, can be used as hybridization probes.

Hybridization assays can be used to detect, prognose, diagnose, or monitor conditions, disorders, or disease states associated with aberrant changes in PARIS-1 expression and/or activity as described supra. In particular, a hybridization assay is carried out by a method comprising contacting a sample containing nucleic acid with a nucleic acid probe capable of hybridizing to PARIS-1 DNA or RNA, under conditions such that hybridization can occur, and detecting or measuring any resulting hybridization.

In specific embodiments, diseases and disorders involving overproliferation of cells can be diagnosed, or their suspected presence can be screened for, or a predisposition to develop such disorders can be detected, in particular prostate cancer or prostate hyperplasia, by detecting increased levels of PARIS-1 protein, PARIS-1 RNA, or PARIS-1 functional activity. Additionally, over proliferation can be diagnosed by detecting mutations in PARIS-1 RNA, DNA or protein (e.g., translocations in PARIS-1 nucleic acids, truncations in the PARIS-1 gene or PARIS-1 protein, changes in nucleotide or amino acid sequence relative to wild-type PARIS-1) that cause increased expression or activity of PARIS-1.

By way of example, levels of PARIS-1 protein in a prostate tumor biopsy can be detected by immunoassay, levels of PARIS-1 RNA can be detected by hybridization assays, e.g., Northern blots, dot blots), translocations and point mutations in PARIS-1 nucleic acids can be detected by Southern blotting, RFLP analysis, PCR using primers that preferably generate a fragment spanning at least most of the PARIS-1 gene, sequencing of the PARIS-1 genomic DNA or cDNA obtained from the sample.

In one embodiment, levels of PARIS-1 mRNA or protein in a sample of prostate tissue isolated from a patient are detected or measured, in which increased levels indicate that the subject has, or has a predisposition to developing, a malignancy or hyperproliferative disorder of the prostate; in which the increased levels are relative to the levels present in an analogous sample from a portion of the body or from a subject not having the malignancy or hyperproliferative disorder, as the case may be.

In another specific embodiment, diseases and disorders involving a deficiency in cell proliferation or in which cell proliferation is desirable for treatment, are diagnosed, or their suspected presence can be screened for, or a predisposition to develop such disorders can be detected, by detecting decreased levels of PARIS-1 protein or PARIS-1 mRNA. Additionally, a deficiency in cell proliferation can be diagnosed by detecting PARIS-1 functional activity, or by detecting mutations in PARIS-1 RNA, DNA or protein (for example, translocations in PARIS-1 nucleic acids, truncations in the gene or protein, changes in nucleotide or amino acid sequence relative to wild-type PARIS-1) that cause decreased expression or activity of PARIS-1. By way of example, levels of PARIS-1 protein, levels of PARIS-1 mRNA, PARIS-1 binding activity, and the presence of translocations or point mutations in PARIS-1 can be determined as described above.

In a specific embodiment, levels of PARIS-1 mRNA or protein in a patient sample are detected or measured, in which decreased levels indicate that the subject has, or has a predisposition to developing, a malignancy or hyperproliferative disorder; in which the decreased levels are relative to the levels present in an analogous sample from a portion of the body or from a subject not having the malignancy or hyperproliferative disorder, as the case may be.

Kits for diagnostic use are also provided, that comprise in one or more containers an anti-PARIS-1 antibody, and, optionally, a labeled binding partner to the antibody. Alternatively, the anti-PARIS-1 antibody can be labeled (with a detectable marker, e.g., a chemiluminescent, enzymatic, fluorescent, or radioactive moiety). A kit is also provided that comprises in one or more containers a nucleic acid probe capable of hybridizing to PARIS-1 mRNA.

In a specific embodiment, a kit can comprise in one or more containers a pair of primers (i.e., each in the size range of 6–30 nucleotides) that are capable of priming amplification (e.g., by polymerase chain reaction (see, for example, Innis et al., *PCR Protocols*, Academic Press, Inc., San Diego, Calif. (1990)), ligase chain reaction (see EP 320,308) use of Q13 replicase, cyclic 5' probe reaction, or other methods known in the art) under appropriate reaction conditions of at least a portion of a PARIS-1 nucleic acid. A kit can optionally further comprise in a container a predetermined amount of a purified PARIS-1 protein or nucleic acid, e.g., for use as a standard or control.

Screening for PARIS-1 Agonists and Antagonists:

PARIS-1 nucleic acids, proteins, and derivatives also have uses in screening assays to detect molecules that specifically bind to PARIS-1 nucleic acids, proteins, or derivatives and thus have potential use as agonists or antagonists of PARIS-1, in particular, molecules that thus affect cell proliferation. In one example, typical assays are performed to screen for molecules with potential utility as anti-cancer drugs or lead compounds for drug development. The invention thus provides assays to detect molecules that specifically bind to PARIS-1 nucleic acids, proteins, or derivatives. For example, recombinant cells expressing PARIS-1 nucleic acids can be used to recombinantly produce PARIS-1 proteins in these assays, to screen for molecules that bind to a PARIS-1 protein. Molecules, (putative binding partners of PARIS-1) are contacted with the PARIS-1 protein (or fragment thereof) under conditions conducive to binding, and then molecules that specifically bind to the PARIS-1 protein are identified. Similar methods can be used to screen for molecules that bind to PARIS-1 protein derivatives or nucleic acids encoding PARIS-1, or a fragment, derivative or analog thereof. Methods that can be used to carry out the foregoing are commonly known in the art, and include diversity libraries, such as random or combinatorial peptide or nonpeptide libraries that can be screened for molecules that specifically bind to PARIS-1. Many libraries are known in the art that can be used, for example, chemically synthesized libraries, recombinant phage display libraries), and in vitro translation-based libraries.

Examples of chemically synthesized libraries are described in Fodor et al., *Science* 251:767–773 (1991); Houghten et al., *Nature* 354:84–86 (1991); Lam et al., *Nature* 354:82–84 (1991); Medynski, *Bio/Technology* 12:709–710 (1994); Gallop et al., *J. Medicinal Chemistry* 37:1233–1251 (1994); Ohlmeyer et al., *Proc. Natl. Acad. Sci. USA* 90:10922–10926 (1993); Erb et al., *Proc. Natl. Acad. Sci. USA* 91:11422–11426 (1994); Houghten et al., *Biotechniques* 13:412 (1992); Jayawickreme et al., *Proc. Natl. Acad. Sci. USA* 91:1614–1618 (1994); Salmon et al., *Proc. Natl. Acad. Sci. USA* 90:11708–11712 (1993); WO 93/20242; and Brenner and Lerner, *Proc. Natl. Acad. Sci. USA* 89:5381–5383 (1992).

Examples of phage display libraries are described in Scott and Smith, *Science* 249:386–390 (1990); Devlin et al., *Science*, 249:404–406 (1990); Christian, et al., 227:711–718 (1992); Lenstra, *J. Immunol. Meth.* 152:149–157 (1992); Kay et al., *Gene* 128:59–65 (1993); and WO 94/18318.

In vitro translation-based libraries include but are not limited to those described in WO 91/05058; and Mattheakis et al., *Proc. Natl. Acad. Sci. USA* 91:9022–9026 (1994). By way of examples of nonpeptide libraries, a benzodiazepine library (see, for example, Bunin et al., *Proc. Natl. Acad. Sci. USA* 91:4708–4712 (1994)) can be adapted for use. Peptoid libraries (Simon et al., *Proc. Natl. Acad. Sci. USA* 89:9367–9371 (1992)) can also be used. Another example of a library that can be used, in which the amide functionalities in peptides have been permethylated to generate a chemically transformed combinatorial library, is described by Ostresh et al., *Proc. Natl. Acad. Sci. USA* 91:11138–11142 (1994).

Screening the libraries can be accomplished by any of a variety of commonly known methods. See, for example, the following references, which disclose screening of peptide libraries: Pannley and Smith, *Adv. Exp. Med. Biol.* 251:215–218 (1989); Scott and Smith, *Science* 249:386–390 (1990); Fowikes et al., *BioTechniques* 13:422–427 (1992); Oldenburg et al., *Proc. Natl. Acad. Sci. USA* 89:5393–5397 (1992); Yu et al., *Cell* 76:933–945 (1994); Staudt et al., *Science* 241:577–580 (1988); Bock et al., *Nature* 355:564–566 (1992); Tuerk et al., *Proc. Natl. Acad. Sci. USA* 89:6988–6992 (1992); Ellington et al., *Nature* 355:850–852 (1992); U.S. Pat. No. 5,096,815, U.S. Pat. No. 5,223,409, and U.S. Pat. No. 5,198,346, all to Ladner et al.; Rebar and Pabo *Science* 263:671–673 (1993); and WO 94/18318.

In a specific embodiment, screening can be carried out by contacting the library members with a PARIS-1 protein (or nucleic acid or derivative) immobilized on a solid phase and harvesting those library members that bind to the protein (or nucleic acid or derivative). Examples of such screening methods, termed "panning" techniques are described by way of example in Parmley and Smith, *Gene* 73:305–318 (1988); Fowlkes et al., *BioTechniques* 13:422–427 (1992); WO 94/18318; and in references cited hereinabove.

In another embodiment, the two-hybrid system for selecting interacting proteins in yeast (Fields and Song, *Nature* 340:245–246 (1989); Chien et al., *Proc. Natl. Acad. Sci. USA* 88:9578–9582 (1991)) can be used to identify molecules that specifically bind to a PARIS-1 protein or derivative.

Animal Models:

The invention also provides animal models. In one embodiment, animal models for diseases and disorders involving cell hypoproliferation are provided herein. Such an animal can be initially produced by promoting homologous recombination between a PARIS-1 gene in its chromosome and an exogenous PARIS-1 gene that has been rendered biologically inactive (typically by insertion of a heterologous sequence, e.g., an antibiotic resistance gene). In one aspect, homologous recombination is carried out by transforming embryo-derived stem (ES) cells with a vector containing the insertionally inactivated PARIS-1 gene, such that homologous recombination occurs, followed by injecting the ES cells into a blastocyst, and implanting the blastocyst into a foster mother, followed by the birth of the chimeric animal ("knockout animal") in which a PARIS-1 gene has been inactivated (see, for example, Capecchi, *Scienice* 244:1288–1292 (1989)). The chimeric animal can be bred to produce additional knockout animals. Such animals can be mice, hamsters, sheep, pigs, cattle, and the like, and are preferably non-human mammals. In a specific embodiment, a knockout mouse is produced. Knockout animals are expected to develop or be predisposed to developing diseases or disorders involving cell hypoproliferation and can be useful to screen for or test molecules for the ability to promote proliferation and thus treat or prevent such diseases and disorders.

In a different embodiment of the invention, transgenic animals that have incorporated and express a functional PARIS-1 gene have use as animal models of diseases and disorders involving cell hyperproliferation or malignancy. Transgenic animals are expected to develop or be predisposed to developing diseases or disorders involving cell hyperproliferation, e.g., malignancy) and thus can have use as animal models of such diseases and disorders, e.g., to screen for or test molecules, e.g., potential anti-cancer agents) for the ability to inhibit overproliferation (e.g., tumor formation) and thus treat or prevent such diseases or disorders.

Thus the invention provides a unique and useful tumor suppressor gene, PARIS-1, having the nucleotide sequence depicted as SEQ ID NO:3 and the PARIS-1 amino acid sequence depicted as SEQ ID NO:4. Nucleotide probes corresponding to all or part of the PARIS-1 cDNA The following examples are provided merely as illustrative of various aspects of the invention and shall not be construed to limit the invention in any way.

EXAMPLE

The following example describes the screening, isolation and characterization of a tumor suppressor gene identified as a prostate cancer associated antigen which appears at high levels in prostatic tissue and is reduced or absent in prostate tumor cell lines and prostate tumor tissues and designated PARIS-1.

Cells Tissues and Sera:

LNCaP (American Type Culture Collection, Manassas, Va. (ATCC) CRL-1740), PC3 (ATCC CRL-1435), DU14S (ATCC HTB-81), and TSU-Pr1 are human prostate cancer cell lines. LNCaP was derived from a hormone refractory prostate cancer patient (Horoszewicz et al., Cancer Res. 43:1809–1818 (1983) (ATCC CRL1740)). PreC is a normal human prostate epithelial cell line. HRE is a normal human renal epithelial cell line. WI-38 (ATCC CCL-75) is a normal human lung fibroblast cell line. These cell lines are routinely maintained.

Prostate tumor tissues and patient sera were obtained from patients who were clinically diagnosed with prostate cancer and were undergoing prostate cancer therapy at Northwest Hospital, Seattle, Wash. Normal sera were obtained from non-tumor-bearing individuals with no prostate cancer history.

Construction of cDNA Expression Libraries:

Complementary DNA expression libraries were constructed from two prostate cancer cell lines, LNCaP (ATCC CRL-1740) and PC3 (ATCC CRL-1435). PolyA+ mRNA was purified from the total cellular RNA isolated from these cells using either a MESSAGE MAKER KIT (GIBCO BRL, Rockville, Md.) or a cDNA synthesis kit (Stratagene, La Jolla, Calif.). The synthesized cDNA was cloned into a lambda ZAP expression vector and the cDNA libraries were constructed using the Lambda ZAP-cDNA GIGAPACK III GOLD CLONING KIT (Stratagene, La Jolla, Calif.).

Immunoscreening of cDNA Libraries:

The cDNA libraries were screened with a pool of sera from 10 patients with prostate cancer diagnosed at clinical stage D2. The screening was performed as described by Sahin et al. (Proc. Natl. Acad Sci USA 92:11810–11813 (1995)) with some modifications. Briefly, recombinant phage at the concentration of 5,000–10,000 pfu/15 cm plate were grown on NZY agar plates for 5 h at 37° C. until the plaques were just visible, and then transferred onto HYBOND-C EXTRA nitrocellulose membranes (Amersham Pharmacia Biotech, Inc. Piscataway, N.J.) pre-soaked with 15 mM IPTG to induce protein expression. After an additional 4–5 h incubation at 37° C., the membranes were removed from the plates, rinsed briefly with phosphate-buffered saline (pH 7.5) containing 0.05% (v/v) Tween 20 (PBST), and blocked with 5% (w/v) non-fat dry milk in PBST for at least 1 h at room temperature or at 4° C. overnight. The membranes were then incubated with the pool of sera diluted 1:250 in PBST for 1–3 h at room temperature. Following 3 washes with PBST, 10 min each time, the membranes were incubated with an alkaline phosphatase (AP)-conjugated, Fc fragment-specific goat anti-human IgG (Sigma, St. Louis, Mo.) at a dilution of 1:10,000 for 1 h at room temperature. The positive plaques were visualized by staining the membranes with 4-nitro blue tetrazolium chloride/5-bromo-4-chloro-3-indolyl-phosphate (NBT/BCIP) (Pierce, Rockford, Ill.) for color development. Following 2–3 more rounds of subcloning, positive plaques were cloned to homogeneity.

Sequence Analysis:

Positive cDNA clones were converted to pBK-CMV phagemid forms by in vivo excision following the procedure described in the instructions of the Lambda ZAP-cDNA GIGAPACK III GOLD CLONING KIT (Stratagene, La Jolla, Calif.). Plasmid DNA was purified by using a plasmid MIDI-PREP KIT (Primm Labs, Inc., Cambridge, Mass.). The cDNA inserts were analyzed by EcoRI/XhoI restriction mapping, and clones with different cDNA inserts were sequenced using a prism automated DNA sequencer (Applied Biosystems Inc.). The cDNA sequences of the identified positive clones were compared to all known genes and the expressed sequence tags (EST) in the GenBank nucleotide and amino acid sequence database, using the BLAST similarity search program. In addition, the gene sequences were analyzed using the GCG sequence analysis program package.

RNA Isolation:

Total cellular RNA was isolated from the cultured cells using TRIzol® RNA isolation reagent (GIBCO BRL, Rockville, Md.). The integrity of the isolated RNA was assessed by formaldehyde-agarose gel electrophoresis, and the quantity of the RNA was determined by measuring the optical density (OD) of the RNA solution at 260 nm.

Probe Preparation and Labeling:

The hPARIS-1 cDNA probe used in Northern blot hybridization is an approximately 1.1 kb PstI fragment. The length and position of the probe is shown in FIG. 1. Briefly, plasmids containing hPARIS-1 cDNA inserts were digested with PstI restriction enzyme for 2–3 h at 37° C. The digested 1.1 kb hPARIS-1 PstI fragment was separated from the vector by electrophoresis on a 1% agarose gel and visualized by UV after a brief staining with ethidium bromide. The insert DNA was extracted from the gel using GENECLEAN II Kit (Bio 101, Inc., La Jolla, Calif.). For a full reaction of probe labeling, 50 ng of hPARIS-1 probe in 31 μl H₂O was denatured at 95° C. for 10 min and chilled on ice immediately for 3 min. Denatured probe DNA was then labeled with $^{32}$P-dCTP (3,000 Ci/mmol, NEN, Boston, Mass.) using an Oligolabeling kit (Amersham Pharmacia Biotech, Inc. Piscataway, N.J.).

The labeling reaction was carried out for 1 h at 37° C. or 4–5 h at room temperature. Unincorporated $^{32}$P-dCTP after reaction was removed by centrifugation of the reaction mixture through a Sephadex G-25 column spun at 4,000 rpm for 5 min in a microcentrifuge. An aliquot of 1 µl labeled DNA was diluted in 3 ml of scintillation fluid and counted in a Beckman LS6500 Multi-purpose Scintillation Counter (Beckman, Fullerton, Calif.). The specific activity of the labeled DNA was determined as cpm/µg DNA, and all probes were primed to a specific activity of $0.5–1.0 \times 10^9$ cpm/(µg DNA. Radiolabeled probe was then mixed with 1 ml of hybridization solution, denatured at 95° C. for 15 min, and cooled on ice immediately for 5 min before used for hybridization.

Northern Blot Analysis:

Twenty micrograms of total cellular RNA was fractionated by electrophoresis in a 1% formaldehyde-agarose gel, transferred onto MAGNAGRAPH nylon membranes (MSI, Westbotough, Mass.) in 20×SSC (1×SSC contains 150 mM NaCl and 15 mM sodium citrate), and fixed by UV irradiation for 5 min. Membranes were pre-incubated at 42° C. for >1 h in a hybridization solution containing 6×SSC, 2×Denhardt's solution, 1 µg/ml denatured salmon sperm DNA, 50% formamide and 2% SDS. The membranes were then hybridized for 16–24 h at 42° C. with $^{32}$P-labeled cDNA probes. After hybridization, the membranes were washed sequentially with 2×SSC/0.1% SDS at 42° C. for 20 min, 0.1×SSC/0.1% SSD at 42° C. for 20 min. and 0.1×SSC/0.1% SDS at 55° C. for 20 min. The hybridized mRNA was visualized by either autoradiography using BioMax X-ray film (Sigma, St. Louis, Mo.) followed by quantification densitometric scanning of the hybridized bands on a IS-1000 Digital Imaging System (Alpha Innotech Corp., San Leandro, Calif.), or visualized and quantified on a PhosphorImager® SI (Molecular Dynamics, Sunnyvale, Calif.) phosphorescence imaging system.

Figure 2:
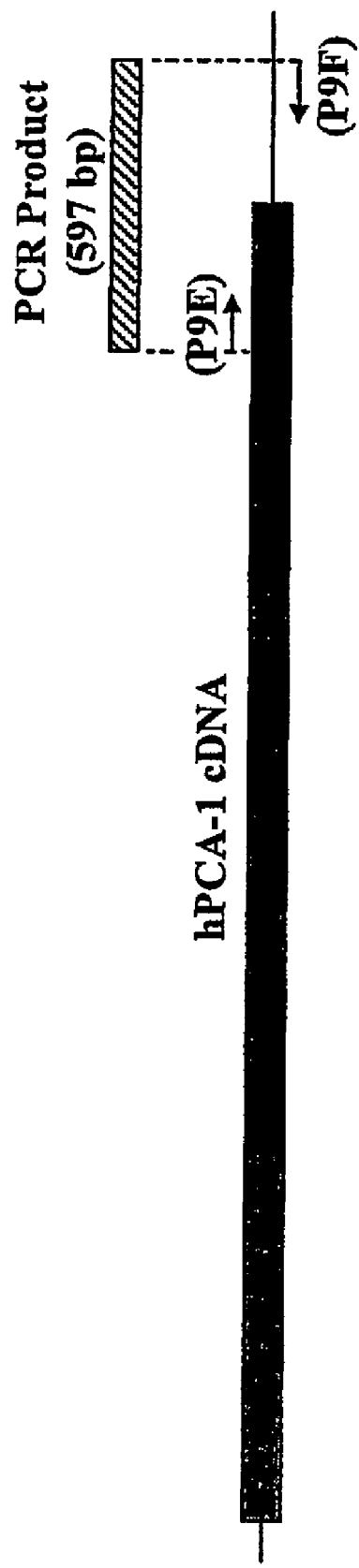
FIG. 2 is a schematic representation of the human PARIS-1 cDNA structure and the location of the human PARIS-1 primers used in RT-PCR. The sequences of the primers P9E (SEQ ID NO: 1) and P9F (SEQ ID NO: 2) and the predicted size of the PCR product are shown.

PCR Primers:

Primers for amplifying hPARIS-1 cDNA was designed based on the cloned hPARIS-1 cDNA sequence, and synthesized by Integrated DNA Technologies, Inc. (Coralville, Iowa). The sequences of the hPARIS-1 primers were: P9E, 5'-GGACGAAGTACAACGAGAAG-3' (SEQ ID NO: 1); P9F, 5'-TACCCTATAGAGGCAGTGCT-3' (SEQ ID NO:2). This set of primers amplifies a 597 bp cDNA fragment near the 3'-end of the hPARIS-1 cDNA. The relative locations of the P9E and P9F primers and the predicted PCR product are shown in FIG. 2.

Reverse Transcription-Polymerase Chain Reaction (RT-PCR):

RT-PCR reactions were performed using a GENEAMP RNA PCR kit (Perkin-Elmer Cetus, Norwalk, Conn.) per the manufacturer's instructions with some modifications. Briefly, three micrograms of total cellular RNA from normal and tumor tissues was transcribed into cDNA by oligo dT priming in a total volume of 20 µl. The synthesized cDNA was used as templated for amplifying hPARIS-1. PCR reactions were performed in a volume of 25 µl solution containing 2 µl of the synthesized cDNA, 1×PCR buffer, 1.5 mM MgCl$_2$, 0.25 mM dNTPs, 0.4 µM each primer, and 2.5 U AMPLITAQ DNA polymerase. The reaction mixture was denatured at 94° C. for 3 min followed by 35 cycles of amplification, with each cycle containing 94° C. for 30 sec, 55° C. for 30 sec, and 72° C. for 30 sec. After a final 10 min extension at 72° C., the reaction mixture was cooled to 4° C. until further processing. For analyzing PCR products, 5 µl of PCR products was electrophoresed on a 1.5% agarose gel and visualized by ethidium bromide staining.

Results

Identification of Prostate Antigens by Allogeneic Patient Sera:

To express prostate antigens in E. coli for SEREX screening, two cDNA expression libraries were constructed from prostate cancer cell lines. The first library was from LNCaP and the second from the PC3 cell line. Two pools of sera from patients diagnosed with prostate cancer at stage D2 were used to screen the constructed libraries. Pool #1 contained 10 patient sera, and both LNCaP and PC3 libraries, comprising approximately $2 \times 10^5$ recombinant phage clones from each library were screened. Pool #2 contained 20 patient sera. Approximately $1 \times 10^5$ phage clones from the LNCaP library were screened with pool #2 sera. The screening resulted in the detection of a total of 6 positive clones from the LNCaP library and 11 positive clones from the PC3 library. Subsequent analyses by restriction digestion, sequencing, and individual serum reaction revealed that the 6 LNCaP-derived positive clones contained the inserts derived from 2 different genes, and the 11 PC3-derived positive clones contained the inserts representing 6 different genes. Identical restriction patterns were observed for clones designated P9, P12 and P22. Therefore, clones P9, P12 and P22 represent the same gene transcripts.

Reaction of Positive Clones to Individual Patient Serum:

The number of patient sera in the serum pool that contain antibodies reactive with clones P9, P12 and P22 were determined by testing patient serum individually for their reactivity to each clone. Two patient sera were found to contain antibody reactive with these clones. No positive reaction was observed when a pool of 10 sera from normal individuals was used to react with each positive clone, and when a negative clone was used to react with each individual patient serum confirming the specificity of the positive reactions observed between the positive clones and the patient sera.

Identities of the Positive Clones:

Clones P9, P12, and P22 were subcloned to homogeneity, and the nucleotide sequences of the cDNA inserts were determined. The similarity if the identified clones to the known genes in the GenBank database was searched using the BLAST similarity search program. The nucleotide sequence of clones P9, P12 and P22 (designated PARIS-1) were not found to be similar to any previously characterized gene.

The hPARIS-1 cDNA was found to be 3,256 base pairs (bp) in length and contains a complete open reading frame of 2,751 bp extending from nucleotide position 93 to 2843 (SEQ ID NO: 3) encoding a primary translation product of 917 amino acids (SEQ ID NO: 4). The relative mass of the putative protein was estimated to be approximately 104 kDa. The nucleotide sequence flanking the ATG at position 93 (SEQ ID NO: 3) (ATG$^{93}$) resembles the consensus sequence for functional initiation codons defined by Kozak (Nuc. Acids Res. 9:5233–5262 (1981), Kozak, J. Mol. Biol. 196: 947–950 (1987)). It is likely that ATG$^{93}$ is the initiation codon for translation in vivo. Analysis of the putative protein sequence for post-translational modification revealed 5 potential N-linked glycosylation sites including 2 cAMP/cGMP-dependent protein kinase phosphorylation sites, 10 protein kinase C phosphorylation sites 11 casein kinase II phosphorylation sites and 1 tyrosine kinase phosphorylation sites (Table 1). The calculated pI of the predicted hPARIS-1 protein is 8.7.

TABLE 1

Posttranslational Modification Sites on bPARIS-1 Protein.

| Posttranslational modification sites | Amino acid positions (SEQ ID NO: 4) | Conserved amino acids |
|---|---|---|
| N-linked glycosylation Sites | 205–207 | NIS |
| | 288–290 | NNT |
| | 301–303 | NRT |
| | 675–677 | NRT |
| | 706–708 | NPT |
| cAMP-and cGMP-dependent protein kinase phosphorylation sites | 343–346 | KRAS |
| | 896–899 | RRAS |
| Protein kinase C phosphorylation sites | 21–23 | SAR |
| | 121–123 | TLK |
| | 207–209 | SLK |
| | 267–269 | SPK |
| | 324–326 | SQK |
| | 391–393 | SLR |
| | 422–424 | SEK |
| | 768–770 | SEK |
| | 848–850 | SRK |
| | 899–901 | SRR |
| Casin kinase II phosphorylation sites | 21–24 | SARD |
| | 83–86 | TAQD |
| | 231–234 | TGHE |
| | 303–306 | TAQE |
| | 324–327 | SQKE |
| | 391–394 | SLRE |
| | 558–561 | SKYD |
| | 567–570 | TVPD |
| | 690–693 | SFPD |
| | 756–759 | SQVD |
| | 910–913 | SEDE |
| Tyrosine kinase phosphorylation sites | 808–815 | RVWDAFLY |

Expression of hPARIS-1 mRNA in Human Prostate Cancer Cells:

The steady-state level of hPARIS-1 mRNA in prostate cancer cells was determined by Northern blot hybridization analysis on total cellular RNA samples from 4 prostate cancer cell lines, LNCaP, PC3, DU14S, and TSU-Pr1. The levels of hPARIS-1 mRNA expression in the prostate cancer cells were compared to those in a normal prostate epithelial cell line, PreC, and in a normal non-prostate cell line, WI-38 (a fetal lung cell line).

Cloned hPARIS-1 cDNA was used as a probe and detected a single species of approximate 3.3 kb mRNA in normal prostate cells. However, this mRNA was almost completely absent in LNCaP and PC3 cells. TSU-Pr1 cells also showed a reduced level of hPARIS-1 mRNA expression. Only DU 145 cells expressed hPARIS-1 mRNA at a level similar to the normal prostate cell PreC. The non-prostate cell line WI-38 expressed a lower level of hPARIS-1 mRNA compared to the normal prostate cells. These results indicated that the hPARIS-1 gene is predominantly expressed in prostate cells, and this expression is lost or reduced in some prostate cancer cells.

Expression of hPARIS-1 mRNA in normal and Tumor Tissues:

The expression of hPARIS-1 mRNA was determined in vivo in prostate cancer patients by RT-PCR and compared to that in normal prostate. Also, the expression of hPARIS-1 mRNA in other types of normal and tumor tissues was determined. Six prostate tissue samples were analyzed for hPARIS-1 expression, including 1 normal prostate tissue RNA (Clontech Laboratories, Inc.) and 5 prostate tissue samples from patients clinically diagnosed with prostate cancer. Of the five prostate cancer patient tissue samples, 3 (#145, #158 and #195) were obtained through radical prostatectomy from patients diagnosed with prostatic adenocarcinoma. Histopathological staining of these samples demonstrated high grade Gleason scores (#145, 5+3=8/10; #195, 4+5=9/10). Prostate sample #188 was obtained from the prostatic adenocarcinoma patient with Gleason grade 4+3=7/10. However, the RNA used for RT-PCR was isolated from the marginal area outside the tumor loci. Prostate sample #197 was obtained through radical cystectomy from a patient with bladder carcinoma, but no carcinogenesis in the prostate.

High level hPARIS-1 mRNA expression was detected from normal prostate tissue samples as indicated by a strong band of amplified PCR product. In contrast, samples from prostate cancer patients (#145, #158, #195, and #188) or bladder cancer patient (#197) demonstrated either a complete absence of hPARIS-1 expression (#145 and #158) or reduced expression (#197, #188, and #197), suggesting a loss of hPARIS-1 expression during carcinogenesis of the prostate. These results obtained from prostate tumor tissue samples were consistent with the results obtained from the prostate cancer cell lines provided above.

Other types of normal and tumor tissues demonstrated different levels of hPARIS-1 mRNA expression. Strong expression of hPARIS-1 mRNA was detected in normal brain tissue, but no expression was detected in a brain tumor tissue sample. Other normal tissues examined demonstrated detectable levels of hPARIS-1 expression, including liver, kidney, heart and colon. Tumor tissues, however, demonstrated a tendency to low or no hPARIS-1 mRNA expression.

Discussion

Northern blot analysis of human PARIS-1 (hPARIS-1) expression demonstrated a loss of human PARIS-1 expression in prostate cancer cell lines LNCaP and PC3, and a reduced expression in TSU-Pr1. This suggests that human PARIS-1 acts as a tumor suppressor gene whose expression may play an important role in maintaining the homeostatic growth of prostate cells in vivo.

Since the SEREX technology is based on the presence of protein antigen in cancer cells and the corresponding antibody produced in the serum of the cancer patient, the results that hPARIS-1 mRNA expression is almost absent in PC3 raised the question how the hPARIS-1 gene was identified from PC3 cells. The result of Northern blot analysis with a hPARIS-1 probe demonstrated a substantial loss of hPARIS-1 mRNA expression in PC3 cells. However, the expression of hPARIS-1mRNA may not be completely suppressed. There is still a very faint hybridization band present in PC3 and LNCaP RNA samples, indicating that a very small amount of mRNA is expressed in these cells. Since the sensitivity of Northern blot hybridization is usually lower than other techniques such as RT-PCR, a trace amount of mRNA detectable by Northern blot hybridization may actually represent a fairly good numbers of mRNA copies in the RNA sample. A single copy of cDNA from the library used correctly cloned into the phage vector is sufficient for the expression of the protein for antibody recognition because the number of cDNA copy is amplified during the infection of host bacteria. Therefore, the trace amount of hPARIS-1 mRNA expressed in PC3 cells is sufficient for SEREX screening.

---

What is claimed is:

1. An isolated nucleic acid comprising the nucleotide sequence encoding a PARIS-1 protein comprising the amino acid sequence of SEQ ID NO: 4, or the full complement thereof.

2. An isolated nucleic acid consisting of at least 25 contiguous nucleotides of the nucleotide sequence of SEQ ID NO: 3 spanning nucleotides 93–2843, or the full complement thereof.

3. An isolated polypeptide having the amino acid sequence of SEQ ID NO: 4.

4. An isolated nucleic acid comprising the nucleotide sequence of SEQ ID NO: 3, or the full complement thereof.

5. An isolated nucleic acid consisting of at least 25 contiguous nucleotides of the coding sequence of a polynucleotide encoding a PARIS-1 protein comprising the amino acid sequence of SEQ ID NO: 4, or the full complement thereof.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 1
ggacgaagta caacgagaag                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 2
taccctatag aggcagtgct                                              20

<210> SEQ ID NO 3
<211> LENGTH: 3256
<212> TYPE: DNA
<213> ORGANISM: Homo sapiens
<220> FEATURE:
<221> NAME/KEY: CDS
<222> LOCATION: (93)..(2843)

<400> SEQUENCE: 3 ctcccttttgg gaagctgccc gccgagtctc cgagatttgt ccctggtggt cccgcggacc     60
cctcgtccct ccgcagtctc cggctggcag cg atg gag ggc gct ggg gag aac      113
                                    Met Glu Gly Ala Gly Glu Asn
                                     1               5 gcc ccg gag tcc agc tcc tct gcc cct ggg tcc gaa gag tct gcc agg      161
Ala Pro Glu Ser Ser Ser Ser Ala Pro Gly Ser Glu Glu Ser Ala Arg
            10                  15                  20 gat cca cag gtg ccg cct ccg gag gaa gaa tcg ggg gac tgc gcc cgg      209
Asp Pro Gln Val Pro Pro Pro Glu Glu Glu Ser Gly Asp Cys Ala Arg
        25                  30                  35 tcc ctg gag gcg gtc ccc aag aaa ctc tgt ggg tat tta agt aag ttc      257
Ser Leu Glu Ala Val Pro Lys Lys Leu Cys Gly Tyr Leu Ser Lys Phe
 40                  45                  50                  55 ggc ggc aaa ggg ccc atc cgg ggc tgg aaa tcc cgc tgg ttc ttc tac      305
Gly Gly Lys Gly Pro Ile Arg Gly Trp Lys Ser Arg Trp Phe Phe Tyr
                 60                  65                  70 gac gaa agg aaa tgt cag ctg tat tac tcg cgg acc gct cag gat gcc      353
Asp Glu Arg Lys Cys Gln Leu Tyr Tyr Ser Arg Thr Ala Gln Asp Ala
             75                  80                  85 aat ccc ttg gac agc atc gac ctc tcc agt gca gtg ttt gac tgt aag      401
Asn Pro Leu Asp Ser Ile Asp Leu Ser Ser Ala Val Phe Asp Cys Lys
         90                  95                 100 gcg gac gct gag gag ggg atc ttc gaa atc aag act ccc agc cgg gtt      449
Ala Asp Ala Glu Glu Gly Ile Phe Glu Ile Lys Thr Pro Ser Arg Val
    105                 110                 115
```

-continued

| | | |
|---|---|---|
| att acc ctg aag gcc gcc acc aag caa gcg atg ctg tac tgg ctg cag<br>Ile Thr Leu Lys Ala Ala Thr Lys Gln Ala Met Leu Tyr Trp Leu Gln<br>120              125              130              135 | 497 |
| cag ctg cag atg aag cgc tgg gaa ttc cac aac agc ccg ccg gca cct<br>Gln Leu Gln Met Lys Arg Trp Glu Phe His Asn Ser Pro Pro Ala Pro<br>                140              145              150 | 545 |
| cct gcc acc cct gat gcc gcc ctg gct ggg aat ggg ccc gtc ctg cac<br>Pro Ala Thr Pro Asp Ala Ala Leu Ala Gly Asn Gly Pro Val Leu His<br>155              160              165 | 593 |
| ctc gag cta ggg caa gaa gag gca gag ctg gag gag ttc ctg tgc cct<br>Leu Glu Leu Gly Gln Glu Glu Ala Glu Leu Glu Glu Phe Leu Cys Pro<br>       170              175              180 | 641 |
| gtg aaa aca ccc cct ggg cta gtg ggc gtg gca gct gcc ttg cag ccc<br>Val Lys Thr Pro Pro Gly Leu Val Gly Val Ala Ala Ala Leu Gln Pro<br>185              190              195 | 689 |
| ttc cct gcc ctt cag aat att tcc ctc aag cac ctg ggg act gaa ata<br>Phe Pro Ala Leu Gln Asn Ile Ser Leu Lys His Leu Gly Thr Glu Ile<br>200              205              210              215 | 737 |
| cag aac aca atg cac aac atc cgt ggc aac aag cag gcc cag gga aca<br>Gln Asn Thr Met His Asn Ile Arg Gly Asn Lys Gln Ala Gln Gly Thr<br>                220              225              230 | 785 |
| ggc cat gaa cct cca ggg gaa gat tct cca cag agt ggg gag cct cag<br>Gly His Glu Pro Pro Gly Glu Asp Ser Pro Gln Ser Gly Glu Pro Gln<br>       235              240              245 | 833 |
| agg gag gag cag ccc ttg gcc tct gac gcc agc acc cca ggg aga gag<br>Arg Glu Glu Gln Pro Leu Ala Ser Asp Ala Ser Thr Pro Gly Arg Glu<br>       250              255              260 | 881 |
| cca gag gat tct cca aag cct gca ccc aag cct tct ctg acc atc agt<br>Pro Glu Asp Ser Pro Lys Pro Ala Pro Lys Pro Ser Leu Thr Ile Ser<br>265              270              275 | 929 |
| ttc gct cag aaa gcc aag cgc cag aac aac acc ttc cca ttc ttt tct<br>Phe Ala Gln Lys Ala Lys Arg Gln Asn Asn Thr Phe Pro Phe Phe Ser<br>280              285              290              295 | 977 |
| gaa gga atc aca cgg aac cga act gcc cag gag aaa gtg gca gcc ttg<br>Glu Gly Ile Thr Arg Asn Arg Thr Ala Gln Glu Lys Val Ala Ala Leu<br>                300              305              310 | 1025 |
| gag caa cag gtt ctg atg ctc acc aag gag tta aag tct cag aag gag<br>Glu Gln Gln Val Leu Met Leu Thr Lys Glu Leu Lys Ser Gln Lys Glu<br>       315              320              325 | 1073 |
| cta gtg aag atc ctg cac aag gca ctg gag gcc gcc cag cag gag aag<br>Leu Val Lys Ile Leu His Lys Ala Leu Glu Ala Ala Gln Gln Glu Lys<br>       330              335              340 | 1121 |
| cgg gcg tcc agc gca tac ctg gcg gcg gct gag gac aag gac cgg ctg<br>Arg Ala Ser Ser Ala Tyr Leu Ala Ala Ala Glu Asp Lys Asp Arg Leu<br>345              350              355 | 1169 |
| gag ctg gtg cgg cac aaa gtg cgg cag atc gcg gag ctg ggc cgg cgg<br>Glu Leu Val Arg His Lys Val Arg Gln Ile Ala Glu Leu Gly Arg Arg<br>360              365              370              375 | 1217 |
| gtg gag gcc ctg gag cag gag cgg gag agc ctg gcg cac aca gcg agc<br>Val Glu Ala Leu Glu Gln Glu Arg Glu Ser Leu Ala His Thr Ala Ser<br>                380              385              390 | 1265 |
| ctg cgg gag cag cag gtg cag gag cta cag cag cac gtg cag ctg ctt<br>Leu Arg Glu Gln Gln Val Gln Glu Leu Gln Gln His Val Gln Leu Leu<br>       395              400              405 | 1313 |
| atg gac aag aac cac gcc aag cag cag gtc atc tgc aag ctc tct gag<br>Met Asp Lys Asn His Ala Lys Gln Gln Val Ile Cys Lys Leu Ser Glu<br>       410              415              420 | 1361 |
| aag gtc acc cag gac ttc acg cac ccc cct gac cag tct cct ttg cgc<br>Lys Val Thr Gln Asp Phe Thr His Pro Pro Asp Gln Ser Pro Leu Arg<br>425              430              435 | 1409 |

-continued

| | |
|---|---|
| ccc gac gct gcc aac agg gac ttc ctg agc cag cag ggg aag ata gag<br>Pro Asp Ala Ala Asn Arg Asp Phe Leu Ser Gln Gln Gly Lys Ile Glu<br>440                 445                450                455 | 1457 |
| cac ctg aag gat gac atg gaa gct tac cgg acc cag aac tgc ttc ctc<br>His Leu Lys Asp Asp Met Glu Ala Tyr Arg Thr Gln Asn Cys Phe Leu<br>460                465               470 | 1505 |
| aac ttc gag atc cac cag gtc aca aag atc tgg aga aag gtg gct gag<br>Asn Phe Glu Ile His Gln Val Thr Lys Ile Trp Arg Lys Val Ala Glu<br>475                480               485 | 1553 |
| aag gag aag gcc ctt ctg acg aag tgc gcc tac ctc caa gcc aga aac<br>Lys Glu Lys Ala Leu Leu Thr Lys Cys Ala Tyr Leu Gln Ala Arg Asn<br>490                495               500 | 1601 |
| tgc cag gtg gaa agc aag tac ctg gcc ggt ctg aga agg ctg cag gag<br>Cys Gln Val Glu Ser Lys Tyr Leu Ala Gly Leu Arg Arg Leu Gln Glu<br>505                510               515 | 1649 |
| gcc ctg ggg gac gaa gcc agc gag tgc tca gag ctg ctg agg cag ctt<br>Ala Leu Gly Asp Glu Ala Ser Glu Cys Ser Glu Leu Leu Arg Gln Leu<br>520                525               530                535 | 1697 |
| gtc cag gag gca ctg cag tgg gaa gct ggg gag gcc tca tct gac agc<br>Val Gln Glu Ala Leu Gln Trp Glu Ala Gly Glu Ala Ser Ser Asp Ser<br>540                545               550 | 1745 |
| atc gag ctg agc ccc atc agt aag tat gat gag tac ggc ttc ctg acg<br>Ile Glu Leu Ser Pro Ile Ser Lys Tyr Asp Glu Tyr Gly Phe Leu Thr<br>555                560               565 | 1793 |
| gtg ccc gac tat gag gtg gaa gac ctg aag ctg ctg gcc aag atc cag<br>Val Pro Asp Tyr Glu Val Glu Asp Leu Lys Leu Leu Ala Lys Ile Gln<br>570                575               580 | 1841 |
| gca ttg gag tca cga tcc cac cac ctg ctg ggc ctc gag gct gtg gat<br>Ala Leu Glu Ser Arg Ser His His Leu Leu Gly Leu Glu Ala Val Asp<br>585                590               595 | 1889 |
| cgg ccg ctg agg gag cgc tgg gct gcc ctg ggc gat ctt gtg ccc tca<br>Arg Pro Leu Arg Glu Arg Trp Ala Ala Leu Gly Asp Leu Val Pro Ser<br>600                605               610               615 | 1937 |
| gcc gag ctc aag cag cta ctg cgg gca gga gta ccc cgt gaa cac cgg<br>Ala Glu Leu Lys Gln Leu Leu Arg Ala Gly Val Pro Arg Glu His Arg<br>620                625               630 | 1985 |
| cct cgt gtc tgg agg tgg ctg gtc cac ctc cgt gtc cag cac ctg cac<br>Pro Arg Val Trp Arg Trp Leu Val His Leu Arg Val Gln His Leu His<br>635                640               645 | 2033 |
| act cca ggc tgc tac cag gaa ctg ctg agc cgg ggc cag gcc cgc gag<br>Thr Pro Gly Cys Tyr Gln Glu Leu Leu Ser Arg Gly Gln Ala Arg Glu<br>650                655               660 | 2081 |
| cac cct gct gcc cgc cag att gag ctg gac ctg aac cgg acc ttc ccc<br>His Pro Ala Ala Arg Gln Ile Glu Leu Asp Leu Asn Arg Thr Phe Pro<br>665                670               675 | 2129 |
| aac aac aaa cac ttc acc tgc ccc acc tcc agc ttc ccc gac aag ctc<br>Asn Asn Lys His Phe Thr Cys Pro Thr Ser Ser Phe Pro Asp Lys Leu<br>680                685               690               695 | 2177 |
| cgc cgg gtg ctg ctg gcc ttc tcc tgg cag aac ccc acc atc ggc tac<br>Arg Arg Val Leu Leu Ala Phe Ser Trp Gln Asn Pro Thr Ile Gly Tyr<br>700                705               710 | 2225 |
| tgc cag ggc ctg aac agg ctg gcg gcc att gcc ctg gtc cta gag<br>Cys Gln Gly Leu Asn Arg Leu Ala Ala Ile Ala Leu Leu Val Leu Glu<br>715                720               725 | 2273 |
| gag gag gag agc gcc ttc tgg tgc ctg gtg gcc att gtg gag acc atc<br>Glu Glu Glu Ser Ala Phe Trp Cys Leu Val Ala Ile Val Glu Thr Ile<br>730                735               740 | 2321 |

-continued

```
atg ccc gct gat tac tac tgc aac acg ctg acg gca tcc cag gtg gac    2369
Met Pro Ala Asp Tyr Tyr Cys Asn Thr Leu Thr Ala Ser Gln Val Asp
745                 750                 755 cag cgg gtg ctc cag gac ctg ctc tcg gag aag ctg ccc agg ctg atg    2417
Gln Arg Val Leu Gln Asp Leu Leu Ser Glu Lys Leu Pro Arg Leu Met
760                 765                 770                 775 gcc cat ctg ggg cag cac cac gtg gat ctc tcc ctc gtc acc ttc aac    2465
Ala His Leu Gly Gln His His Val Asp Leu Ser Leu Val Thr Phe Asn
                780                 785                 790 tgg ttc ctc gtg gtc ttt gcg gac agt ctc att agc aac atc ctc ctt    2513
Trp Phe Leu Val Val Phe Ala Asp Ser Leu Ile Ser Asn Ile Leu Leu
            795                 800                 805 cgg gtc tgg gat gcc ttc ctg tac gag ggg acg aag tac aac gag aag    2561
Arg Val Trp Asp Ala Phe Leu Tyr Glu Gly Thr Lys Tyr Asn Glu Lys
        810                 815                 820 gag atc ttg agg cta cag aat ggc ctg gaa atc tac cag tac ctg cgc    2609
Glu Ile Leu Arg Leu Gln Asn Gly Leu Glu Ile Tyr Gln Tyr Leu Arg
825                 830                 835 ttc ttc acc aag acc atc tcc aac agc cgg aag ctg atg aac atc gcc    2657
Phe Phe Thr Lys Thr Ile Ser Asn Ser Arg Lys Leu Met Asn Ile Ala
840                 845                 850                 855 ttc aat gac atg aac ccc ttc cgc atg aaa cag ctg cgg cag ctg cgc    2705
Phe Asn Asp Met Asn Pro Phe Arg Met Lys Gln Leu Arg Gln Leu Arg
                860                 865                 870 atg gtc cac cgg gag cgg ctg gag gct gag ctg cgg gag ctg gag cag    2753
Met Val His Arg Glu Arg Leu Glu Ala Glu Leu Arg Glu Leu Glu Gln
            875                 880                 885 ctt aag gca gag tac ctg gag agg cgg gca tcc cgg cgc aga gct gtg    2801
Leu Lys Ala Glu Tyr Leu Glu Arg Arg Ala Ser Arg Arg Arg Ala Val
        890                 895                 900 tcc gag ggc tgt gcc agc gag gac gag gtg gag ggg gaa gcc             2843
Ser Glu Gly Cys Ala Ser Glu Asp Glu Val Glu Gly Glu Ala
905                 910                 915 tgacttggcc acctcccctc cccacagcct tcctcaccct tggctggcag acccactgga   2903
ggtcaggcac ggaccagtgg cccagccctg ggtgtcccat caccatgtga ccttggacat   2963
gtcccttccc ctctctggcc ctcagtttcc ccactgggac attgtgtgct gcaaagccat   3023
tggttgggct acttcttcat aggcacttac ttacccaggg atgccaccct ttcgtcacct   3083
cttccacaga gcactttggc atgtaaacaa gcaagagcac tgcctctata gggtaacctg   3143
gaacattctc taggttatat caatataaaa caatgtaaat ggtggaaaaa aaaaaaaaa    3203 aaaaaaaaa aaaaaaaaa aaaaaaaaa aaaaaaaaa aaaaaaaaa aaa              3256
```

<210> SEQ ID NO 4
<211> LENGTH: 917
<212> TYPE: PRT
<213> ORGANISM: Homo sapiens

<400> SEQUENCE: 4

```
Met Glu Gly Ala Gly Glu Asn Ala Pro Glu Ser Ser Ser Ala Pro
1               5                   10                  15

Gly Ser Glu Glu Ser Ala Arg Asp Pro Gln Val Pro Pro Glu Glu
                20                  25                  30

Glu Ser Gly Asp Cys Ala Arg Ser Leu Glu Ala Val Pro Lys Lys Leu
            35                  40                  45

Cys Gly Tyr Leu Ser Lys Phe Gly Gly Lys Gly Pro Ile Arg Gly Trp
        50                  55                  60
```

```
Lys Ser Arg Trp Phe Phe Tyr Asp Glu Arg Lys Cys Gln Leu Tyr Tyr
 65                  70                  75                  80

Ser Arg Thr Ala Gln Asp Ala Asn Pro Leu Asp Ser Ile Asp Leu Ser
                 85                  90                  95

Ser Ala Val Phe Asp Cys Lys Ala Asp Ala Glu Glu Gly Ile Phe Glu
            100                 105                 110

Ile Lys Thr Pro Ser Arg Val Ile Thr Leu Lys Ala Ala Thr Lys Gln
            115                 120                 125

Ala Met Leu Tyr Trp Leu Gln Gln Leu Gln Met Lys Arg Trp Glu Phe
130                 135                 140

His Asn Ser Pro Pro Ala Pro Pro Ala Thr Pro Asp Ala Ala Leu Ala
145                 150                 155                 160

Gly Asn Gly Pro Val Leu His Leu Glu Leu Gly Gln Glu Glu Ala Glu
                165                 170                 175

Leu Glu Glu Phe Leu Cys Pro Val Lys Thr Pro Pro Gly Leu Val Gly
            180                 185                 190

Val Ala Ala Ala Leu Gln Pro Phe Pro Ala Leu Gln Asn Ile Ser Leu
            195                 200                 205

Lys His Leu Gly Thr Glu Ile Gln Asn Thr Met His Asn Ile Arg Gly
210                 215                 220

Asn Lys Gln Ala Gln Gly Thr Gly His Glu Pro Pro Gly Glu Asp Ser
225                 230                 235                 240

Pro Gln Ser Gly Glu Pro Gln Arg Glu Glu Gln Pro Leu Ala Ser Asp
                245                 250                 255

Ala Ser Thr Pro Gly Arg Glu Pro Glu Asp Ser Pro Lys Pro Ala Pro
            260                 265                 270

Lys Pro Ser Leu Thr Ile Ser Phe Ala Gln Lys Ala Lys Arg Gln Asn
            275                 280                 285

Asn Thr Phe Pro Phe Phe Ser Glu Gly Ile Thr Arg Asn Arg Thr Ala
290                 295                 300

Gln Glu Lys Val Ala Ala Leu Glu Gln Gln Val Leu Met Leu Thr Lys
305                 310                 315                 320

Glu Leu Lys Ser Gln Lys Glu Leu Val Lys Ile Leu His Lys Ala Leu
                325                 330                 335

Glu Ala Ala Gln Gln Glu Lys Arg Ala Ser Ser Ala Tyr Leu Ala Ala
            340                 345                 350

Ala Glu Asp Lys Asp Arg Leu Glu Leu Val Arg His Lys Val Arg Gln
            355                 360                 365

Ile Ala Glu Leu Gly Arg Arg Val Glu Ala Leu Glu Gln Glu Arg Glu
370                 375                 380

Ser Leu Ala His Thr Ala Ser Leu Arg Glu Gln Gln Val Gln Glu Leu
385                 390                 395                 400

Gln Gln His Val Gln Leu Leu Met Asp Lys Asn His Ala Lys Gln Gln
                405                 410                 415

Val Ile Cys Lys Leu Ser Glu Lys Val Thr Gln Asp Phe Thr His Pro
            420                 425                 430

Pro Asp Gln Ser Pro Leu Arg Pro Asp Ala Ala Asn Arg Asp Phe Leu
            435                 440                 445

Ser Gln Gln Gly Lys Ile Glu His Leu Lys Asp Asp Met Glu Ala Tyr
450                 455                 460

Arg Thr Gln Asn Cys Phe Leu Asn Phe Glu Ile His Gln Val Thr Lys
465                 470                 475                 480
```

-continued

```
Ile Trp Arg Lys Val Ala Glu Lys Glu Lys Ala Leu Leu Thr Lys Cys
            485                 490                 495
Ala Tyr Leu Gln Ala Arg Asn Cys Gln Val Glu Ser Lys Tyr Leu Ala
            500                 505                 510
Gly Leu Arg Arg Leu Gln Glu Ala Leu Gly Asp Glu Ala Ser Glu Cys
            515                 520                 525
Ser Glu Leu Leu Arg Gln Leu Val Gln Glu Ala Leu Gln Trp Glu Ala
            530                 535                 540
Gly Glu Ala Ser Ser Asp Ser Ile Glu Leu Ser Pro Ile Ser Lys Tyr
545                 550                 555                 560
Asp Glu Tyr Gly Phe Leu Thr Val Pro Asp Tyr Glu Val Glu Asp Leu
                565                 570                 575
Lys Leu Leu Ala Lys Ile Gln Ala Leu Glu Ser Arg Ser His His Leu
            580                 585                 590
Leu Gly Leu Glu Ala Val Asp Arg Pro Leu Arg Glu Arg Trp Ala Ala
            595                 600                 605
Leu Gly Asp Leu Val Pro Ser Ala Glu Leu Lys Gln Leu Leu Arg Ala
            610                 615                 620
Gly Val Pro Arg Glu His Arg Pro Arg Val Trp Arg Trp Leu Val His
625                 630                 635                 640
Leu Arg Val Gln His Leu His Thr Pro Gly Cys Tyr Gln Glu Leu Leu
                645                 650                 655
Ser Arg Gly Gln Ala Arg Glu His Pro Ala Ala Arg Gln Ile Glu Leu
            660                 665                 670
Asp Leu Asn Arg Thr Phe Pro Asn Asn Lys His Phe Thr Cys Pro Thr
            675                 680                 685
Ser Ser Phe Pro Asp Lys Leu Arg Arg Val Leu Leu Ala Phe Ser Trp
            690                 695                 700
Gln Asn Pro Thr Ile Gly Tyr Cys Gln Gly Leu Asn Arg Leu Ala Ala
705                 710                 715                 720
Ile Ala Leu Leu Val Leu Glu Glu Glu Ser Ala Phe Trp Cys Leu
                725                 730                 735
Val Ala Ile Val Glu Thr Ile Met Pro Ala Asp Tyr Tyr Cys Asn Thr
            740                 745                 750
Leu Thr Ala Ser Gln Val Asp Gln Arg Val Leu Gln Asp Leu Leu Ser
            755                 760                 765
Glu Lys Leu Pro Arg Leu Met Ala His Leu Gly Gln His His Val Asp
            770                 775                 780
Leu Ser Leu Val Thr Phe Asn Trp Phe Leu Val Val Phe Ala Asp Ser
785                 790                 795                 800
Leu Ile Ser Asn Ile Leu Leu Arg Val Trp Asp Ala Phe Leu Tyr Glu
                805                 810                 815
Gly Thr Lys Tyr Asn Glu Lys Glu Ile Leu Arg Leu Gln Asn Gly Leu
            820                 825                 830
Glu Ile Tyr Gln Tyr Leu Arg Phe Phe Thr Lys Thr Ile Ser Asn Ser
            835                 840                 845
Arg Lys Leu Met Asn Ile Ala Phe Asn Asp Met Asn Pro Phe Arg Met
850                 855                 860
Lys Gln Leu Arg Gln Leu Arg Met Val His Arg Glu Arg Leu Glu Ala
865                 870                 875                 880
Glu Leu Arg Glu Leu Glu Gln Leu Lys Ala Glu Tyr Leu Glu Arg Arg
                885                 890                 895
```

-continued

```
Ala Ser Arg Arg Arg Ala Val Ser Glu Gly Cys Ala Ser Glu Asp Glu
            900                 905                 910

Val Glu Gly Glu Ala
        915
```